US009889239B2

(12) United States Patent
Michaels et al.

(10) Patent No.: US 9,889,239 B2
(45) Date of Patent: Feb. 13, 2018

(54) FLUID COLLECTION AND DISPOSAL SYSTEM AND RELATED METHODS

(75) Inventors: Thomas L. Michaels, McCullom Lake, IL (US); Russell A. Johnson, Spring Grove, IL (US); Eric D. Hill, Gurnee, IL (US); Hetal Patel, Libertyville, IL (US); Brian T. Leadingham, Pleasant Prarie, WI (US)

(73) Assignee: ALLEGIANCE CORPORATION, Waukegan, IL (US)

( * ) Notice: Subject to any disclaimer, the term of this patent is extended or adjusted under 35 U.S.C. 154(b) by 220 days.

(21) Appl. No.: 13/010,021

(22) Filed: Jan. 20, 2011

(65) Prior Publication Data

US 2011/0178482 A1  Jul. 21, 2011

Related U.S. Application Data

(63) Continuation-in-part of application No. 12/837,297, filed on Jul. 15, 2010, now Pat. No. 8,460,256, which
(Continued)

(51) Int. Cl.
*A61M 1/00* (2006.01)
*A61M 27/00* (2006.01)

(52) U.S. Cl.
CPC ........ *A61M 1/0001* (2013.01); *A61M 1/0017* (2014.02); *A61M 1/0049* (2013.01); *A61M 27/00* (2013.01)

(58) Field of Classification Search
CPC .......... A61F 5/441; A61F 5/44; A61F 5/4405; A61F 5/4404; A61G 9/00; A61M 1/0019;
(Continued)

(56) References Cited

U.S. PATENT DOCUMENTS 687,790 A  12/1901 Scales
1,703,834 A  2/1929 Thompson
(Continued)

FOREIGN PATENT DOCUMENTS

CN  1199192  11/1998
CN  1398468 A  2/2003
(Continued)

OTHER PUBLICATIONS

Baatz, S. et al., Hand off Support for mobility with IP over Bluetooth, Univ of Bonn, Inst. of Computer Sci IV (2000 IEEE), pp. 143-154.
(Continued)

*Primary Examiner* — Tatyana Zalukaeva
*Assistant Examiner* — Benjamin Klein
(74) *Attorney, Agent, or Firm* — Jacob R. Lenzke

(57) ABSTRACT

A fluid collection system includes a disposable collection container configured to receive a disposable collection container. The fluid collection container may include a flexible liner configured to collapse during evacuation of the fluid from the liner. The system may include a receiving housing sized to receive the disposable collection container, the receiving housing including a cavity and a piston assembly positioned within the cavity, the piston including a piston check valve. The system includes a suction source connectable to the disposable collection container and a filter positioned between the suction source and the cavity. A first connecting line extends between a suction source opening, configured to communicate the suction source to the disposable collection container, and the filter. A first check valve connects to the first connecting line between the suction source opening and the filter.

22 Claims, 27 Drawing Sheets

Related U.S. Application Data is a continuation-in-part of application No. 12/076,842, filed on Mar. 24, 2008, now Pat. No. 8,500,706.

(60) Provisional application No. 61/362,326, filed on Jul. 8, 2010, provisional application No. 61/225,812, filed on Jul. 15, 2009, provisional application No. 60/919,607, filed on Mar. 23, 2007, provisional application No. 60/963,325, filed on Aug. 3, 2007.

(58) Field of Classification Search
CPC .............. A61M 1/0001; A61M 1/0013; A61M 1/0023; A61M 2001/0017; A61M 1/0005; A61M 1/008; A61M 1/0017; A61M 27/00; A61M 1/0049; A61B 10/007
USPC ........ 604/319, 317, 323, 324; 210/741, 806, 210/435; 600/581
See application file for complete search history.

(56) References Cited

U.S. PATENT DOCUMENTS

| | | |
|---|---|---|
| 2,057,238 A | 10/1936 | Krug |
| 2,452,503 A | 10/1948 | Teetor |
| 2,686,625 A | 8/1954 | Sundholm |
| 3,035,623 A | 5/1962 | Goetz |
| 3,164,186 A | 1/1965 | Weber et al. |
| 3,164,600 A | 1/1965 | Janssen |
| 3,307,746 A | 3/1967 | Edwards |
| 3,397,648 A * | 8/1968 | Henderson ................. 417/207 |
| 3,515,127 A | 6/1970 | Reymond |
| 3,537,455 A | 11/1970 | Skyles et al. |
| 3,699,815 A | 10/1972 | Legrand |
| 3,719,197 A | 3/1973 | Pannier et al. |
| 3,745,999 A | 7/1973 | Deaton |
| 3,768,478 A | 10/1973 | Ashley et al. |
| 3,773,211 A | 11/1973 | Bridgman |
| 3,780,738 A | 12/1973 | Deaton |
| 3,804,090 A | 4/1974 | Holbrook |
| 3,805,788 A | 4/1974 | Kleiner |
| 3,814,098 A | 6/1974 | Deaton |
| 3,830,238 A | 8/1974 | Kurtz et al. |
| 3,843,016 A | 10/1974 | Bornhorst et al. |
| 3,878,962 A | 4/1975 | Holbrook et al. |
| 3,915,189 A | 10/1975 | Holbrook et al. |
| 3,924,772 A | 12/1975 | Magnani |
| 3,945,392 A | 3/1976 | Deaton et al. |
| 4,015,603 A | 4/1977 | Kurtz et al. |
| 4,022,258 A | 5/1977 | Steidley |
| 4,173,295 A | 11/1979 | Steinman |
| 4,181,140 A | 1/1980 | Ammann et al. |
| 4,245,637 A | 1/1981 | Nichols |
| 4,275,731 A | 6/1981 | Nichols |
| 4,275,732 A | 6/1981 | Gereg |
| 4,321,922 A | 3/1982 | Deaton |
| 4,340,049 A | 7/1982 | Munsch |
| 4,346,711 A | 8/1982 | Agdanowski et al. |
| 4,347,946 A | 9/1982 | Nichols |
| 4,348,711 A | 9/1982 | Else et al. |
| 4,379,455 A | 4/1983 | Deaton |
| 4,392,860 A | 7/1983 | Huck et al. |
| 4,397,643 A | 8/1983 | Rygiel |
| 4,419,093 A | 12/1983 | Deaton |
| 4,455,140 A | 6/1984 | Joslin |
| 4,460,361 A | 7/1984 | Nichols |
| D276,464 S | 11/1984 | Weigl et al. |
| 4,492,313 A | 1/1985 | Touzani |
| 4,515,283 A | 5/1985 | Suzuki |
| 4,516,973 A | 5/1985 | Telang |
| 4,541,457 A | 9/1985 | Blenkush |
| 4,568,006 A | 2/1986 | Mueller et al. |
| 4,569,674 A | 2/1986 | Phillips et al. |
| 4,578,060 A | 3/1986 | Huck et al. |
| 4,642,128 A | 2/1987 | Solorzano |
| 4,650,477 A | 3/1987 | Johnson |
| 4,681,571 A * | 7/1987 | Nehring .............. A61M 1/0001 137/205 |
| 4,706,830 A | 11/1987 | Wareing |
| 4,735,610 A | 4/1988 | Akkas et al. |
| 4,769,019 A | 9/1988 | Kerwin |
| 4,773,897 A | 9/1988 | Scheller et al. |
| 4,775,366 A | 10/1988 | Rosenblatt |
| 4,790,453 A | 12/1988 | Fontana et al. |
| 4,798,580 A | 1/1989 | DeMeo et al. |
| 4,799,924 A | 1/1989 | Rosenblatt |
| 4,799,925 A | 1/1989 | Rosenblatt |
| 4,823,833 A | 4/1989 | Hogan et al. |
| 4,863,446 A | 9/1989 | Parker |
| 4,874,023 A | 10/1989 | Ulm |
| 4,888,728 A | 12/1989 | Shirakawa et al. |
| 4,906,261 A | 3/1990 | Mohajer |
| 4,921,679 A | 5/1990 | Martin et al. |
| 4,925,447 A | 5/1990 | Rosenblatt |
| 4,928,245 A | 5/1990 | Moy et al. |
| 4,930,997 A | 6/1990 | Bennett |
| RE33,250 E | 7/1990 | Cook |
| 4,941,689 A | 7/1990 | Sjoeberg |
| 4,948,010 A | 8/1990 | Wiggins |
| 4,950,247 A | 8/1990 | Rosenblatt |
| 4,957,491 A | 9/1990 | Parker |
| 4,957,492 A | 9/1990 | McVay |
| 4,963,134 A | 10/1990 | Bachscheider et al. |
| 4,964,189 A | 10/1990 | Rau et al. |
| 4,976,694 A | 12/1990 | Schreibman |
| 4,979,628 A | 12/1990 | Robbins, III |
| 4,980,913 A | 12/1990 | Skret |
| 4,981,473 A | 1/1991 | Rosenblatt |
| 4,986,839 A | 1/1991 | Wertz et al. |
| 5,002,534 A | 3/1991 | Rosenblatt |
| 5,010,179 A | 4/1991 | Lai |
| 5,014,389 A | 5/1991 | Ogilvie et al. |
| 5,027,963 A | 7/1991 | Robbins, III |
| 5,039,494 A | 8/1991 | Martin et al. |
| 5,071,409 A | 12/1991 | Rosenberg |
| 5,072,762 A | 12/1991 | Jimenz |
| 5,084,250 A | 1/1992 | Hall |
| 5,124,126 A | 6/1992 | Ripp |
| 5,125,891 A | 6/1992 | Hossain et al. |
| 5,149,318 A | 9/1992 | Lindsay |
| 5,156,602 A | 10/1992 | Steffler |
| 5,163,900 A | 11/1992 | Wortrich |
| 5,173,442 A | 12/1992 | Carey |
| 5,178,828 A | 1/1993 | Uesugi |
| 5,185,007 A * | 2/1993 | Middaugh et al. ........... 604/320 |
| 5,192,272 A | 3/1993 | Faure |
| 5,209,565 A | 5/1993 | Goncalves |
| 5,217,038 A | 6/1993 | Pinder |
| 5,217,688 A | 6/1993 | Von Lersner |
| 5,234,419 A | 8/1993 | Bryant et al. |
| 5,242,434 A | 9/1993 | Terry |
| 5,242,474 A | 9/1993 | Herbst et al. |
| 5,252,290 A | 10/1993 | Uesugi |
| 5,254,080 A | 10/1993 | Lindsay |
| 5,256,160 A | 10/1993 | Clement |
| 5,267,956 A | 12/1993 | Beuchat |
| 5,268,666 A | 12/1993 | Michel et al. |
| 5,269,030 A | 12/1993 | Pahno et al. |
| 5,279,602 A | 1/1994 | Middaugh et al. |
| 5,295,518 A | 3/1994 | Baker et al. |
| 5,309,924 A | 5/1994 | Peabody |
| 5,318,516 A | 6/1994 | Cosmescu |
| 5,330,464 A | 7/1994 | Mathias et al. |
| 5,333,761 A | 8/1994 | Davis et al. |
| 5,336,169 A | 8/1994 | Divilio et al. |
| 5,364,342 A | 11/1994 | Beuchat et al. |
| 5,370,270 A | 12/1994 | Adams et al. |
| 5,380,289 A | 1/1995 | Hemstreet et al. |
| 5,399,156 A | 3/1995 | Lindsay |
| 5,417,655 A | 5/1995 | Divilio et al. |
| 5,423,779 A | 6/1995 | Yeh |
| 5,438,721 A | 8/1995 | Pahno et al. |
| 5,470,324 A | 11/1995 | Cook et al. |
| 5,494,074 A | 2/1996 | Ramacier, Jr. et al. |
| 5,514,119 A | 5/1996 | Curtis |

(56) References Cited

U.S. PATENT DOCUMENTS

| | | |
|---|---|---|
| 5,519,858 A | 5/1996 | Walton et al. |
| 5,520,668 A | 5/1996 | Greff et al. |
| 5,522,808 A | 6/1996 | Skalla |
| 5,526,956 A | 6/1996 | Osgar |
| 5,549,585 A | 8/1996 | Maher et al. |
| 5,551,001 A | 8/1996 | Cohen et al. |
| 5,588,167 A | 12/1996 | Pahno et al. |
| 5,607,411 A | 3/1997 | Heironimus et al. |
| 5,620,428 A | 4/1997 | Hand |
| 5,634,896 A | 6/1997 | Bryant et al. |
| 5,637,103 A | 6/1997 | Kerwin et al. |
| 5,645,540 A | 7/1997 | Henniges et al. |
| 5,653,270 A | 8/1997 | Burrows |
| 5,669,892 A | 9/1997 | Keogh et al. |
| 5,683,371 A | 11/1997 | Hand |
| 5,685,835 A | 11/1997 | Brugger |
| 5,688,255 A | 11/1997 | Hand |
| 5,720,078 A | 2/1998 | Heintz |
| 5,741,237 A | 4/1998 | Walker |
| 5,741,238 A | 4/1998 | Bradbury et al. |
| 5,755,705 A | 5/1998 | Van Driel |
| 5,776,118 A | 7/1998 | Seifert et al. |
| 5,776,260 A | 7/1998 | Dunn et al. |
| 5,785,044 A | 7/1998 | Meador et al. |
| 5,792,126 A | 8/1998 | Tribastone et al. |
| 5,797,506 A | 8/1998 | Lehmkuhl et al. |
| 5,807,230 A | 9/1998 | Argenta et al. |
| 5,807,359 A | 9/1998 | Bemis et al. |
| 5,808,885 A | 9/1998 | Dew et al. |
| 5,830,198 A | 11/1998 | Henniges et al. |
| 5,835,723 A | 11/1998 | Andrews et al. |
| 5,836,909 A | 11/1998 | Cosmescu |
| 5,855,289 A | 1/1999 | Moore |
| 5,859,847 A | 1/1999 | Dew et al. |
| 5,867,555 A | 2/1999 | Popescu et al. |
| 5,871,476 A | 2/1999 | Hand |
| 5,885,240 A | 3/1999 | Bradbury et al. |
| 5,901,717 A | 5/1999 | Dunn et al. |
| 5,906,025 A | 5/1999 | Johnson |
| 5,910,291 A | 6/1999 | Skalla et al. |
| 5,914,047 A | 6/1999 | Griffiths |
| 5,919,360 A | 7/1999 | Contaxis, III et al. |
| 5,931,822 A | 8/1999 | Bemis et al. |
| 5,944,703 A | 8/1999 | Dixon et al. |
| 5,945,004 A | 8/1999 | Ohira et al. |
| 5,947,171 A | 9/1999 | Woodruff |
| 5,968,032 A | 10/1999 | Sleister |
| 5,975,096 A | 11/1999 | Dunn et al. |
| 5,985,009 A | 11/1999 | Marsala |
| 5,997,733 A | 12/1999 | Wilbur et al. |
| 6,006,272 A | 12/1999 | Aravamudan et al. |
| 6,017,493 A | 1/2000 | Cambron et al. |
| 6,024,124 A | 2/2000 | Braun et al. |
| 6,027,490 A | 2/2000 | Radford et al. |
| 6,039,724 A | 3/2000 | Seifert et al. |
| 6,045,596 A | 4/2000 | Holland, Jr. et al. |
| 6,056,731 A | 5/2000 | Koetke et al. |
| 6,058,106 A | 5/2000 | Cudak et al. |
| 6,078,952 A | 6/2000 | Fielding et al. |
| 6,082,401 A | 7/2000 | Braun et al. |
| 6,093,230 A | 7/2000 | Johnson, III et al. |
| 6,105,093 A | 8/2000 | Rosner et al. |
| 6,105,638 A | 8/2000 | Edwards et al. |
| 6,115,881 A | 9/2000 | Hult et al. |
| 6,136,098 A | 10/2000 | Tribastone |
| 6,152,902 A | 11/2000 | Christian et al. |
| 6,160,808 A | 12/2000 | Maurya |
| 6,161,578 A | 12/2000 | Braun et al. |
| 6,180,000 B1 | 1/2001 | Wilbur et al. |
| 6,183,453 B1 | 2/2001 | Swisher |
| 6,203,590 B1 | 3/2001 | Byrd et al. |
| 6,222,283 B1 | 4/2001 | Regla |
| 6,231,089 B1 | 5/2001 | DeCler et al. |
| 6,233,248 B1 | 5/2001 | Sautter et al. |
| 6,244,311 B1 | 6/2001 | Hand et al. |
| 6,258,232 B1 | 7/2001 | Hasegawa et al. |
| 6,261,276 B1 | 7/2001 | Reitsma |
| 6,263,887 B1 | 7/2001 | Dunn |
| 6,270,488 B1 | 8/2001 | Johnson et al. |
| 6,280,867 B1 | 8/2001 | Elias |
| 6,331,246 B1 | 12/2001 | Beckham et al. |
| 6,358,232 B1 | 3/2002 | Hand et al. |
| 6,366,583 B2 | 4/2002 | Rowett et al. |
| 6,368,310 B1 | 4/2002 | Bemis et al. |
| 6,415,313 B1 | 7/2002 | Yamada et al. |
| 6,453,687 B2 | 9/2002 | Sharood et al. |
| 6,488,675 B1 | 12/2002 | Radford et al. |
| 6,494,391 B2 | 12/2002 | Mosenson et al. |
| 6,494,869 B1 | 12/2002 | Hand et al. |
| 6,499,495 B2 | 12/2002 | Jeng |
| 6,501,180 B1 | 12/2002 | Kitch |
| 6,507,953 B1 | 1/2003 | Horlander et al. |
| 6,522,654 B1 | 2/2003 | Small |
| 6,524,307 B1 | 2/2003 | Palmerton et al. |
| 6,588,436 B2 | 7/2003 | Dunn et al. |
| 6,615,243 B1 | 9/2003 | Megeid et al. |
| 6,618,764 B1 | 9/2003 | Shteyn |
| 6,626,877 B2 | 9/2003 | Anderson et al. |
| 6,631,476 B1 | 10/2003 | Vandesteeg et al. |
| 6,652,495 B1 | 11/2003 | Walker |
| 6,672,477 B2 | 1/2004 | Miller et al. |
| 6,673,055 B2 | 1/2004 | Bemis et al. |
| 6,676,644 B2 | 1/2004 | Ikeda |
| 6,688,436 B1 | 2/2004 | Wang |
| 6,705,591 B2 | 3/2004 | DeCler |
| 6,706,198 B2 | 3/2004 | Gershenson |
| 6,721,900 B1 | 4/2004 | Lenner et al. |
| 6,731,201 B1 | 5/2004 | Bailey et al. |
| 6,735,619 B1 | 5/2004 | Sawada |
| 6,755,807 B2 | 6/2004 | Risk, Jr. et al. |
| 6,759,946 B2 | 7/2004 | Sahinoglu et al. |
| 6,770,061 B2 | 8/2004 | Wildman |
| 6,776,175 B2 | 8/2004 | Dunn et al. |
| 6,793,222 B2 | 9/2004 | Katsaounis et al. |
| 6,800,074 B2 | 10/2004 | Henley et al. |
| 6,824,533 B2 | 11/2004 | Risk, Jr. et al. |
| 6,842,430 B1 | 1/2005 | Melnik |
| 6,854,053 B2 | 2/2005 | Burkhardt et al. |
| 6,856,999 B2 | 2/2005 | Flanagin et al. |
| 6,891,850 B1 | 5/2005 | Vandesteeg et al. |
| 6,893,425 B2 | 5/2005 | Dunn et al. |
| 6,902,673 B2 | 6/2005 | Smit et al. |
| 6,909,891 B2 | 6/2005 | Yamashita et al. |
| 6,915,444 B2 | 7/2005 | Vasko et al. |
| 6,934,740 B1 | 8/2005 | Lawande et al. |
| 6,976,977 B2 | 12/2005 | Yam |
| 6,982,960 B2 | 1/2006 | Lee et al. |
| 6,987,462 B2 | 1/2006 | Bae et al. |
| 6,987,790 B2 | 1/2006 | Govorkov et al. |
| 7,035,270 B2 | 4/2006 | Moore, Jr. et al. |
| 7,058,722 B2 | 6/2006 | Ikami et al. |
| 7,062,531 B2 | 6/2006 | Kim |
| 7,069,091 B2 | 6/2006 | Williamson |
| 7,090,663 B2 | 8/2006 | Dunn et al. |
| 7,107,358 B2 | 9/2006 | Vasko et al. |
| 7,111,100 B2 | 9/2006 | Ellerbrock |
| 7,114,518 B2 | 10/2006 | Kirby |
| 7,115,115 B2 | 10/2006 | Bemis et al. |
| 7,115,228 B2 | 10/2006 | Lundtveit et al. |
| 7,148,142 B1 | 12/2006 | Dakshina-Murthy et al. |
| 7,149,792 B1 | 12/2006 | Hansen et al. |
| 7,163,618 B2 | 1/2007 | Beckham et al. |
| 7,200,683 B1 | 4/2007 | Wang et al. |
| 7,257,104 B2 | 8/2007 | Shitama |
| 7,258,711 B2 | 8/2007 | Dunn et al. |
| 7,287,062 B2 | 10/2007 | Im et al. |
| 7,294,839 B2 | 11/2007 | Rich et al. |
| 7,308,644 B2 | 12/2007 | Humpleman et al. |
| 7,328,816 B2 | 2/2008 | Shannon et al. |
| 7,353,259 B1 | 4/2008 | Bakke et al. |
| 7,389,332 B1 | 6/2008 | Muchow et al. |
| 7,389,358 B1 | 6/2008 | Matthews et al. |
| 7,403,994 B1 | 7/2008 | Vogl et al. |
| 7,412,538 B1 | 8/2008 | Eytchison et al. |

(56) References Cited

U.S. PATENT DOCUMENTS

| | | |
|---|---|---|
| 7,421,478 B1 | 9/2008 | Muchow |
| 7,430,591 B2 | 9/2008 | Chamberlain |
| 7,437,494 B2 | 10/2008 | Ellerbrock |
| 7,454,517 B2 | 11/2008 | Ha et al. |
| 7,461,164 B2 | 12/2008 | Edwards et al. |
| 7,468,330 B2 | 12/2008 | Allen et al. |
| 7,469,727 B2 | 12/2008 | Marshall |
| 7,481,243 B2 | 1/2009 | Michaels et al. |
| 7,497,340 B2 | 3/2009 | Hershberger et al. |
| 7,673,030 B2 | 3/2010 | Hite et al. |
| 7,673,153 B1 | 3/2010 | Oishi et al. |
| 2001/0025322 A1 | 9/2001 | Song et al. |
| 2002/0011923 A1 | 1/2002 | Cunningham et al. |
| 2002/0021465 A1 | 2/2002 | Moore, Jr. et al. |
| 2002/0026528 A1 | 2/2002 | Lo |
| 2002/0035624 A1 | 3/2002 | Kim |
| 2002/0038358 A1 | 3/2002 | Sweatt, III et al. |
| 2002/0059617 A1 | 5/2002 | Terakado et al. |
| 2002/0082569 A1 | 6/2002 | Wildman |
| 2002/0103898 A1 | 8/2002 | Moyer et al. |
| 2002/0118696 A1 | 8/2002 | Suda |
| 2002/0120763 A1 | 8/2002 | Miloushev et al. |
| 2002/0127780 A1 | 9/2002 | Ma et al. |
| 2002/0165989 A1 | 11/2002 | Etoh |
| 2002/0183702 A1* | 12/2002 | Henley et al. ............... 604/305 |
| 2002/0193144 A1 | 12/2002 | Belski et al. |
| 2003/0009537 A1 | 1/2003 | Wang |
| 2003/0014530 A1 | 1/2003 | Bodin et al. |
| 2003/0014630 A1 | 1/2003 | Spencer et al. |
| 2003/0037166 A1 | 2/2003 | Ueno et al. |
| 2003/0038730 A1 | 2/2003 | Imafuku et al. |
| 2003/0051053 A1 | 3/2003 | Vasko et al. |
| 2003/0051203 A1 | 3/2003 | Vasko et al. |
| 2003/0053477 A1 | 3/2003 | Kim et al. |
| 2003/0054809 A1 | 3/2003 | Bridges et al. |
| 2003/0065824 A1 | 4/2003 | Kudo |
| 2003/0067910 A1 | 4/2003 | Razazian et al. |
| 2003/0079000 A1 | 4/2003 | Chamberlain |
| 2003/0079001 A1 | 4/2003 | Chamberlain |
| 2003/0083758 A1 | 5/2003 | Williamson |
| 2003/0085795 A1 | 5/2003 | An |
| 2003/0088703 A1 | 5/2003 | Kim |
| 2003/0158956 A1 | 8/2003 | Tanaka et al. |
| 2003/0165142 A1 | 9/2003 | Mills et al. |
| 2003/0178360 A1* | 9/2003 | Haldopoulos et al. ....... 210/435 |
| 2004/0023162 A1 | 2/2004 | Hasegawa et al. |
| 2004/0042487 A1 | 3/2004 | Ossman |
| 2004/0047298 A1 | 3/2004 | Yook et al. |
| 2004/0055105 A1 | 3/2004 | Park et al. |
| 2004/0064578 A1 | 4/2004 | Boucher et al. |
| 2004/0088731 A1 | 5/2004 | Putterman et al. |
| 2004/0102743 A1 | 5/2004 | Walker |
| 2004/0111490 A1 | 6/2004 | Im et al. |
| 2004/0116902 A1 | 6/2004 | Grossman et al. |
| 2004/0129338 A1 | 7/2004 | Rohret et al. |
| 2004/0158333 A1 | 8/2004 | Ha et al. |
| 2004/0158388 A1 | 8/2004 | Fujiwara et al. |
| 2004/0164076 A1 | 8/2004 | Baker et al. |
| 2004/0184456 A1 | 9/2004 | Binding et al. |
| 2004/0204603 A1 | 10/2004 | Leconte et al. |
| 2004/0204679 A1 | 10/2004 | Visconti et al. |
| 2004/0204693 A1 | 10/2004 | Anderson et al. |
| 2004/0205309 A1 | 10/2004 | Watanabe |
| 2004/0224261 A1 | 11/2004 | Resnick et al. |
| 2005/0069696 A1 | 3/2005 | King et al. |
| 2005/0108568 A1 | 5/2005 | Bussiere et al. |
| 2005/0139532 A1 | 6/2005 | Hershberger et al. |
| 2005/0170269 A1 | 8/2005 | Nakagawa et al. |
| 2005/0171495 A1 | 8/2005 | Austin et al. |
| 2005/0183780 A1 | 8/2005 | Michaels et al. |
| 2005/0187526 A1 | 8/2005 | Horne |
| 2005/0187528 A1 | 8/2005 | Berg |
| 2005/0187529 A1 | 8/2005 | Reasoner et al. |
| 2005/0189283 A1 | 9/2005 | Smit et al. |
| 2005/0189288 A1 | 9/2005 | Hershberger et al. |
| 2005/0190727 A1 | 9/2005 | Vanlieshout et al. |
| 2005/0202350 A1 | 9/2005 | Colburn et al. |
| 2005/0215961 A1 | 9/2005 | Romano et al. |
| 2005/0250052 A1 | 11/2005 | Nguyen |
| 2005/0267445 A1 | 12/2005 | Mendels |
| 2006/0030681 A1 | 2/2006 | Sawyer et al. |
| 2006/0036219 A1 | 2/2006 | Alvin |
| 2006/0047677 A1 | 3/2006 | Lin et al. |
| 2006/0129092 A1 | 6/2006 | Hanlon et al. |
| 2006/0156836 A1 | 7/2006 | Ny et al. |
| 2006/0156918 A1 | 7/2006 | Dahl |
| 2006/0248518 A1 | 11/2006 | Kundert |
| 2006/0271709 A1 | 11/2006 | Vasko et al. |
| 2007/0019615 A1 | 1/2007 | Baek et al. |
| 2007/0025368 A1 | 2/2007 | Ha et al. |
| 2007/0032058 A1 | 2/2007 | Sung |
| 2007/0038191 A1 | 2/2007 | Burbank et al. |
| 2007/0044439 A1 | 3/2007 | Dunn et al. |
| 2007/0135778 A1 | 6/2007 | Murray et al. |
| 2007/0135779 A1 | 6/2007 | Lalomia et al. |
| 2008/0053539 A1 | 3/2008 | Hershberger et al. |
| 2008/0097631 A1 | 4/2008 | Baek et al. |
| 2008/0222325 A1 | 9/2008 | Ishino et al. |
| 2008/0255692 A1 | 10/2008 | Hofrichter et al. |
| 2008/0259786 A1 | 10/2008 | Gonda |
| 2009/0005747 A1* | 1/2009 | Michaels et al. ............. 604/319 |
| 2009/0012485 A1 | 1/2009 | Michaels et al. |
| 2009/0159535 A1 | 6/2009 | Hershberger et al. |
| 2009/0182263 A1* | 7/2009 | Burbank et al. ............... 604/28 |
| 2011/0313375 A1* | 12/2011 | Michaels ....................... 604/319 |
| 2013/0144232 A1 | 6/2013 | Michaels et al. |
| 2013/0247326 A1 | 9/2013 | Michaels et al. |
| 2013/0341330 A1 | 12/2013 | Michaels et al. |
| 2013/0345651 A1 | 12/2013 | Michaels et al. |

FOREIGN PATENT DOCUMENTS

| | | |
|---|---|---|
| CN | 1398469 | 2/2003 |
| EP | 1 115 263 A1 | 7/2001 |
| EP | 1 202 493 A2 | 5/2002 |
| EP | 1 387 216 A2 | 2/2004 |
| EP | 1387215 A1 | 2/2004 |
| FR | 2808449 A3 | 11/2001 |
| GB | 2 233 494 A | 1/1991 |
| JP | 60-112336 | 6/1985 |
| JP | 61-216543 | 9/1986 |
| JP | 8-500763 | 1/1996 |
| JP | 08-112344 | 5/1996 |
| JP | 9295651 A | 11/1997 |
| JP | 2002-325079 | 11/2002 |
| JP | 2003-519460 | 6/2003 |
| KR | 10-2001-0093265 | 10/2001 |
| KR | 10-2002-0064847 | 8/2002 |
| KR | 20020084847 A | 11/2002 |
| KR | 10-2003-0040766 | 5/2003 |
| WO | WO 80/01558 A1 | 8/1980 |
| WO | WO-9112033 A1 | 8/1991 |
| WO | WO 95/01192 | 1/1995 |
| WO | WO-9517912 A1 | 7/1995 |
| WO | WO 98/55164 A1 | 12/1998 |
| WO | WO 01/03178 A1 | 1/2001 |
| WO | WO-0124846 A1 | 4/2001 |
| WO | WO 01/50825 A1 | 7/2001 |
| WO | WO 01/80030 A1 | 10/2001 |
| WO | WO 02/09350 A3 | 3/2002 |
| WO | WO-02074632 A1 | 9/2002 |
| WO | WO 02/097555 A3 | 12/2002 |
| WO | WO-02097555 A2 | 12/2002 |
| WO | WO 03/030252 A2 | 4/2003 |
| WO | WO 2005/031855 A1 | 4/2005 |
| WO | WO 2008/094703 A2 | 8/2008 |

OTHER PUBLICATIONS

Ganz et al., "Q-Soft: software framework for QoS support in home networks," Computer Nov. 1998, pp. 1-66.

(56) References Cited

OTHER PUBLICATIONS

Hwang et al., "ATM-based plug-and-play technique for in-home networking," Electronics Letters, vol. 34, No. 22, pp. 2088-2090, 1998.
International Search Report & Written Opinion issued in PCT/US2008/03817, dated Jun. 20, 2008 11 pages.
International Search Report issued in PCT/US2008/03818, dated Jul. 30, 2008, 13 pages.
Invitation to Pay Additional Fees & Partial Search Report issued in PCT/US2007/008371, mailed Oct. 29, 2007, 4 pages.
Kent et al., "Security Architecture for the Internet Protocol," Network Working Group, Nov. 1998, pp. 1-66.
Kim et al., "Home Networking Digital TV Based on LnCP," IEEE Transaction on Consumer Electronics, vol. 48, No. 4, Nov. 2002, pp. 990-996.
Lee et al., "A New Control Protocol for Home Appliance LnCP" International Symposium on Industrial Electronics, 2001, Proceedings, ISIE 2001, Jun. 12-16, 2001 pp. 286-291.
Lee et al., "A New Home Network Protocol Controlling and Monitoring Home Appliance-HNCP," IEEE, 2002, pp. 312-313.
Lee et al., "Home Network Control Protocol for Networked Home Appliance and Its Application," IEEE, pp. 1-7, 2002.
Letter from Foreign Associate dated Jun. 26, 2008, with Official Translation of Communication issued in DE 10 2006 030 267.2, dated May 26, 2008, 3 pages.
Letter from Foreign Associate dated Oct. 19, 2007, with Official Translation of Communication issued in DE 10 2006 030 267.2, dated Sep. 13, 2007, 4 pages.
Manner et al., "Evaluation of Mobility and quality of service interaction," The International Journal of Computer and Telecommunications Networking, vol. 38, No. 2, pp. 137-163, 2002.
Neptune 2 Ultra, Waste Management System, 2 pages; as viewed at http://www.stryker.com/stellent/groups/instruments/documents/web_prod/059445.pdf, Feb. 21, 2008, pp. 1-2.
Notice of Rejection issued in Japanese Application No. 2010-500951, mailed Jan. 8, 2013, 4 pages.
Wang et al., "Towards Dependable Home Networking: An Experience Report," IEEE, 2000, pp. 43-48.
Written Opinion of the ISA issued in PCT/US2007/008371, 4 Pages.
"Check valve" entry from McGraw-Hill Dictionary of Engineering, © 1997, The McGraw-Hill Companies Inc.
Ganz, A., et al., "Q-Soft software Framework for QoS Support in Home Networks," Computer Networks 2003, vol. 42, pp. 7-22.
International Search Report and Written Opinion for Application No. PCT/US2008/03818, mailed Jul. 30, 2008, 12 pages.
International Search Report and Written Opinion for Application No. PCT/US2010/042145, mailed Sep. 13, 2010, 8 pages.
"New surgical system from Stryker installed in BCHS operating rooms". Battle Creek Health System. [Retrieved on Feb. 21, 2008] Retrieved from the internet: URL: http://www.bchealth.com/news/stryker.shtml, 2 pages.
Supplementary European Search Report and Search Opinion for European Application No. 08742213.5, mailed on Aug. 8, 2012, 5 pages.
Non-Final Office Action dated Nov. 3, 2015 for U.S. Appl. No. 13/754,571, filed Jan. 30, 2013.

\* cited by examiner

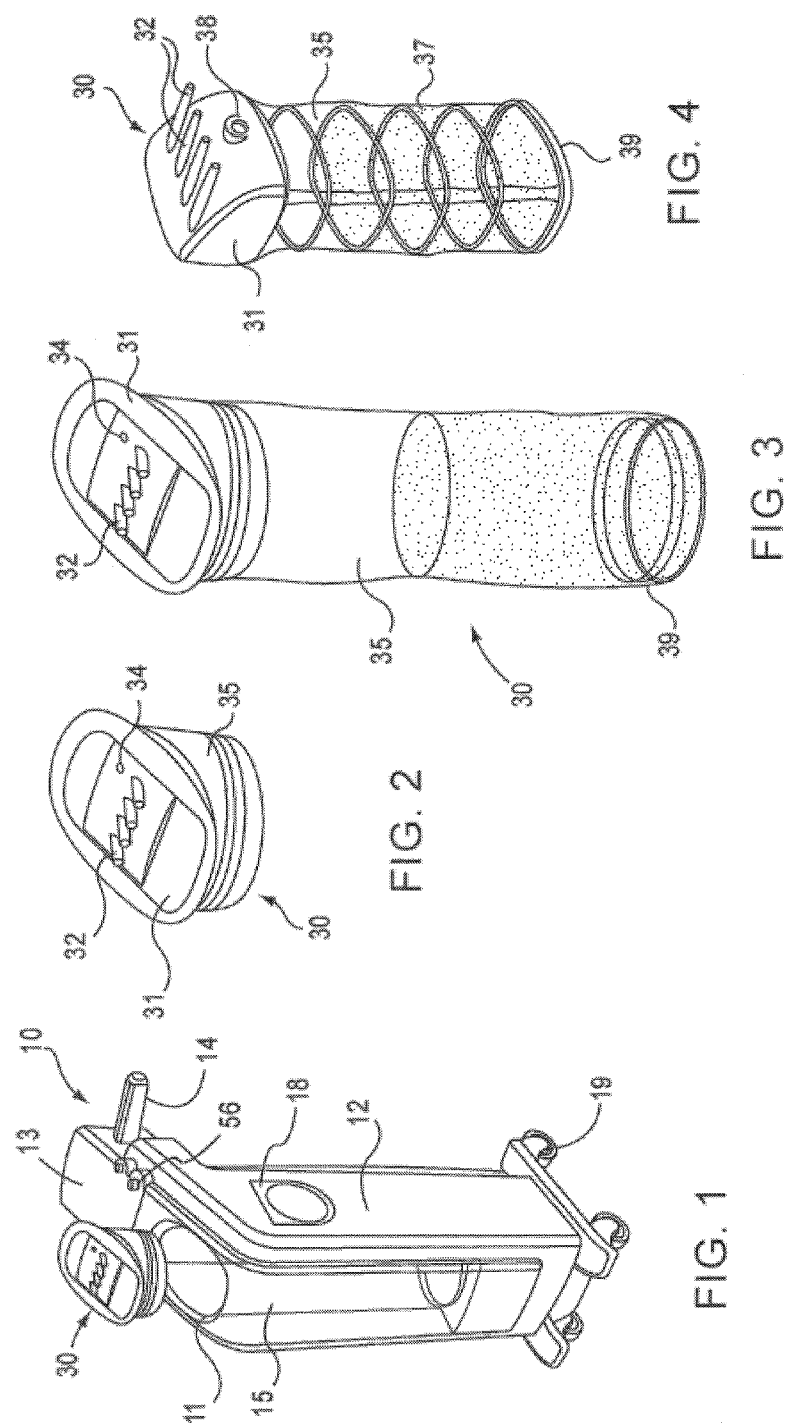

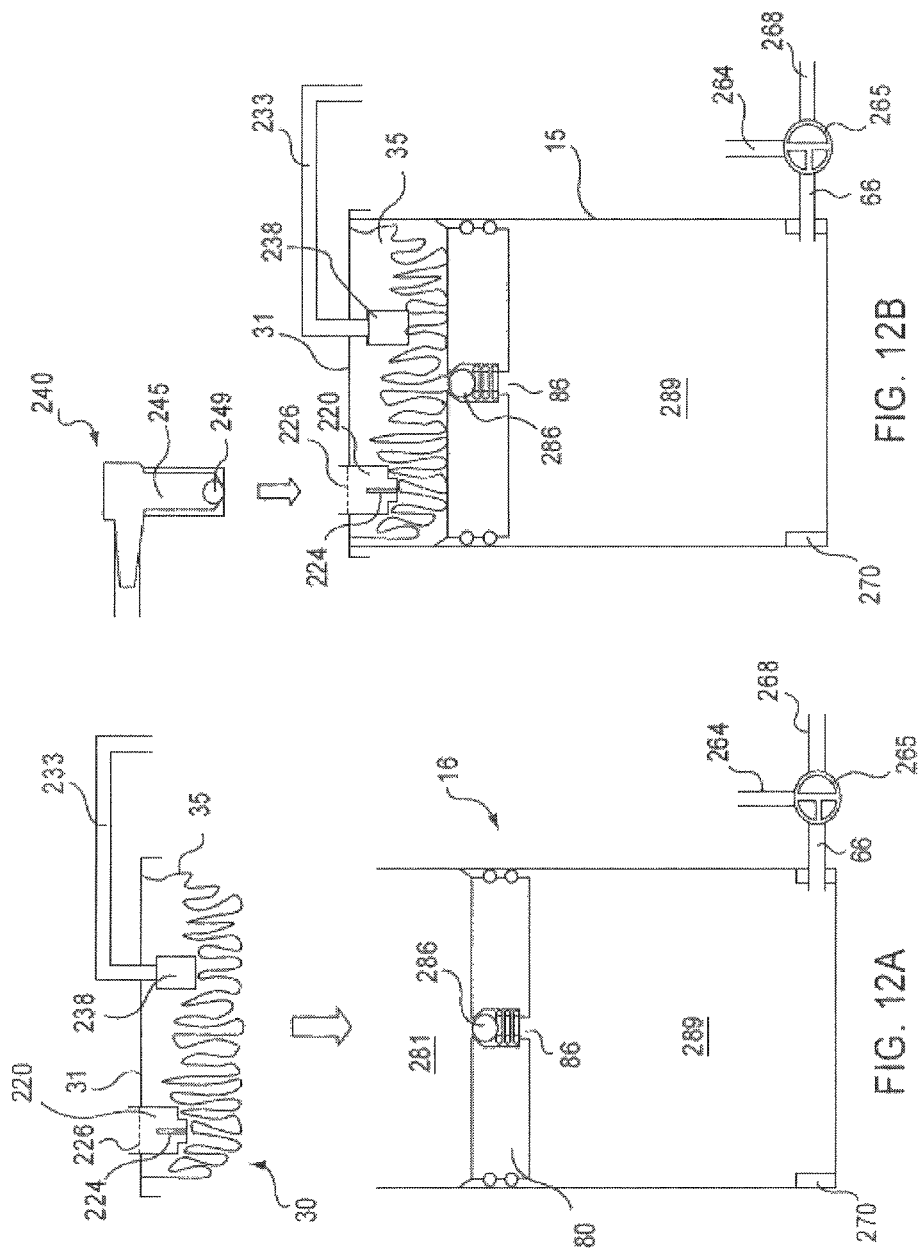

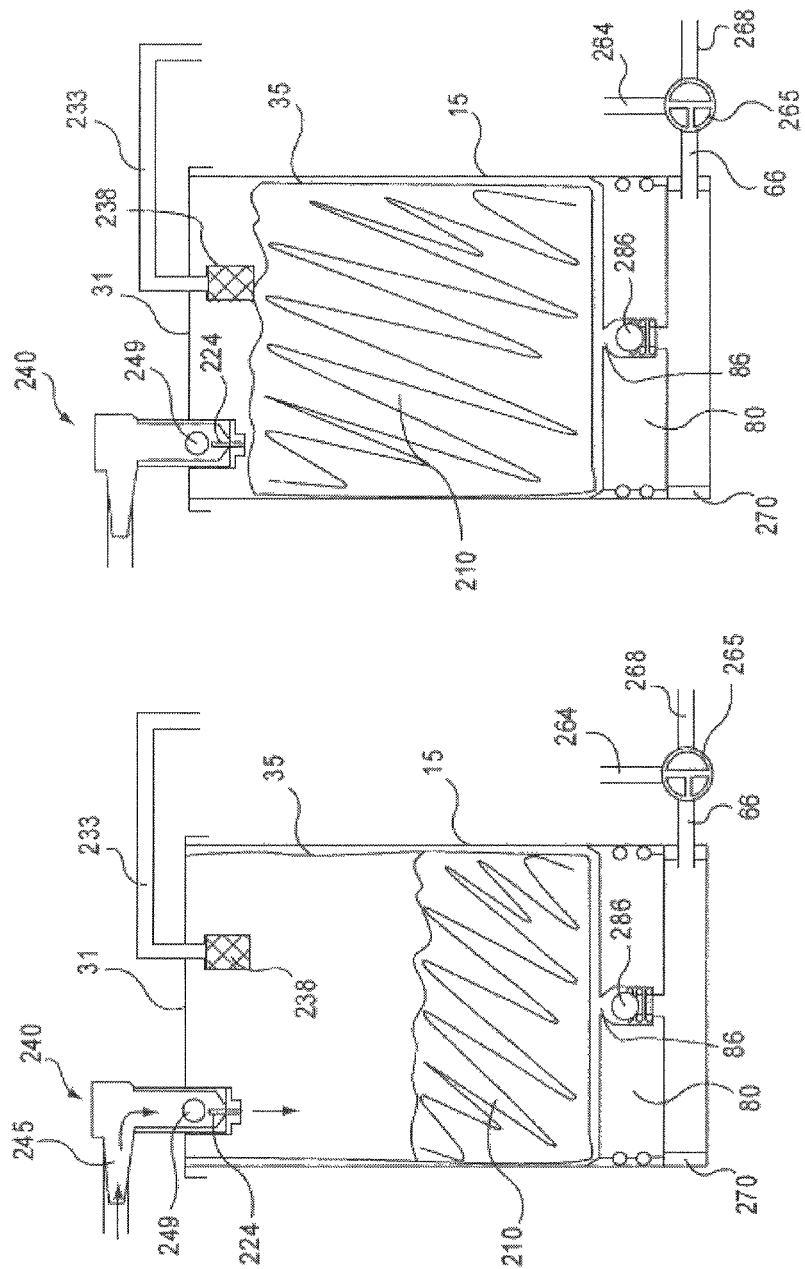

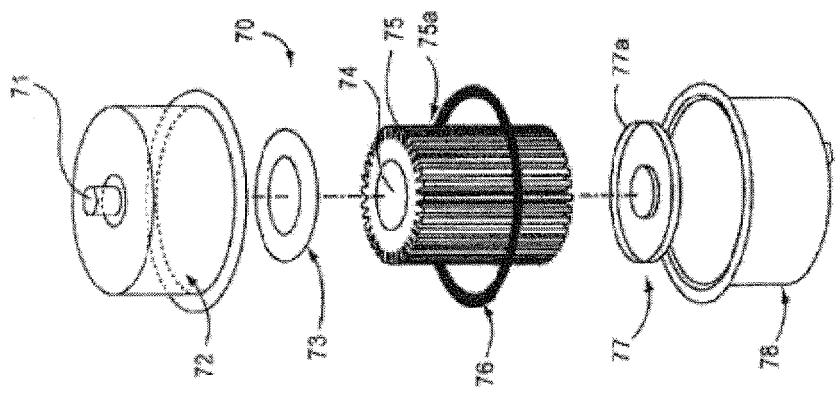
FIG. 28
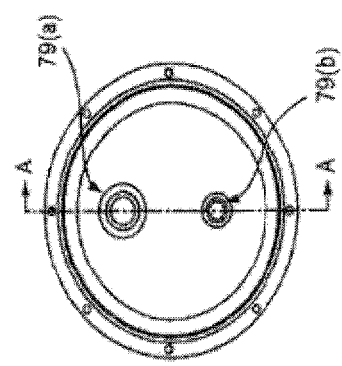
FIG. 27(a)
FIG. 27(b)
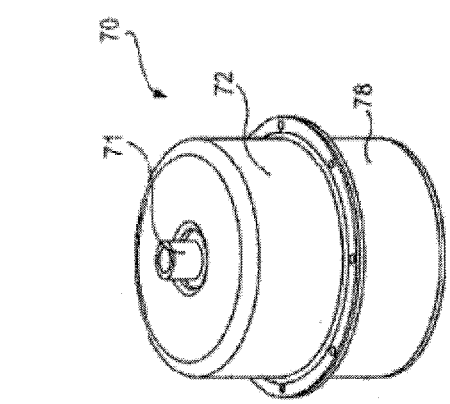
FIG. 26

FLUID COLLECTION AND DISPOSAL SYSTEM AND RELATED METHODS

CLAIM OF PRIORITY UNDER 35 U.S.C. §120 AND §119

The present Application for Patent is a continuation-in-part of patent application Ser. No. 12/837,297, entitled "FLUID COLLECTION AND DISPOSAL SYSTEM AND RELATED METHODS" filed on Jul. 15, 2010, pending, which claims the benefit of priority to U.S. Provisional Application Ser. No. 61/225,812, entitled "FLUID COLLECTION AND DISPOSAL SYSTEM AND RELATED METHODS" and filed on Jul. 15, 2009, the entire contents of both of which are expressly incorporated herein by reference in their entirety. The present application is also a continuation-in-part of patent application Ser. No. 12/076,842, entitled "FLUID COLLECTION AND DISPOSAL SYSTEM HAVING INTERCHANGEABLE COLLECTION AND OTHER FEATURES AND METHODS RELATING THERETO" filed on Mar. 24, 2008, the entire contents of which are expressly incorporated by reference herein in their entirety, pending, which claims the benefit of priority to Provisional Application No. 60/919,607, entitled "LIQUID COLLECTION AND DISPOSAL SYSTEM AND RELATED METHODS" filed on Mar. 23, 2007 and Provisional Application No. 60/963,325, entitled "LIQUID COLLECTION AND DISPOSAL SYSTEM AND RELATED METHODS" filed on Aug. 3, 2007. This application also claims priority to Provisional Application Ser. No. 61/362,326, entitled "FLUID COLLECTION AND DISPOSAL SYSTEM AND RELATED METHODS" filed on Jul. 8, 2010, the entire contents of which are expressly incorporated by reference in their entirety.

BACKGROUND

1. Technical Field

Aspects relate generally to fluid collection and disposal systems and related methods. More specifically, particular aspects relate to liquid collection and disposal systems that utilize flexible liners and related methods of use thereof.

2. Brief Description of Related Art

Hospital operating rooms, emergency rooms, and other healthcare facilities generate a large volume of liquid waste, which may include irrigation liquids and secretions removed from a patient's body (e.g., blood and other bodily liquids). To collect and dispose of such liquid waste, suction canisters are typically used. A typical suction canister is a temporary storage container that uses suction to create a negative pressure inside the canister to drain liquids or secretions from the patients' body. After each medical procedure (e.g., surgery), the canister containing the liquid waste is transported to a utility area to be disposed of as red-bag waste or to be emptied, cleaned, and disinfected for reuse. A new or cleaned canister is then brought into the operating room for a next medical procedure. This process can be labor intensive and time consuming. Furthermore, since this process is performed following every medical procedure, the frequency of the process may increase the clinicians' risk of exposure to potentially hazardous waste.

Accordingly, there is a need for an improved waste collection and disposal system that may overcome one or more of the problems discussed above.

SUMMARY

Among others, various aspects may include providing a fluid collection system that utilizes disposable flexible liners to reduce the volume of medical wastes. Another aspect may include providing a lid for a fluid collection system that automatically connects to a suction source. Also, certain aspects may provide a waste disposal system, for use with the fluid collection system that may improve labor efficiency, safety, and convenience of the medical personnel participating in a medical procedure. In particular, the fluid collection systems and waste disposal systems in accordance with aspects of the present invention may provide a clean and convenient interface between the source of waste and the waste disposal station, thereby reducing the risk of exposure to potentially hazardous waste.

While exemplary aspects will be described in connection with a particular medical waste collection and disposal process, various aspects may be used in other suitable medical and non-medical applications, such as medical or non-medical cleaning devices and processes.

Aspects may include a fluid collection container, including a flexible liner; a lid attached to the flexible liner such that the lid and flexible liner define a substantially sealed interior space therebetween, the lid having: a first opening configured for communication with a first access port of a suction instrument through which the collection container receives fluid; a second opening configured for communication with a second access port of a suction source; a rupturable evacuation port for communication with a disposal station through which collected fluid is removed from the collection container; and a shelf formed on the surface of the lid facing the liner.

Aspects may further include a fluid collection system including a disposable collection container configured to receive a disposable collection container. The system may include a receiving housing sized to receive the disposable collection container, the receiving housing including a cavity and a piston assembly positioned within the cavity, the piston including a piston check valve. The system may include a suction source connectable to the disposable collection container and a filter positioned between the suction source and the cavity. A first connecting line may extend between a suction source opening, configured to communicate the suction source to the disposable collection container, and the filter. A first check valve may connect to the first connecting line between the suction source opening and the filter.

Aspects may further include a fluid trap attached between the filter and the suction source. The cavity may include a bottom opening positioned below the piston assembly, the system further including a second connecting line extending between the bottom opening and the filter, a vent attached to the second connecting line between the bottom opening and the filter, and a second check valve connected to the second connecting line between the vent and the filter.

Aspects may further include a third connecting line attached to the filter, a vacuum regulator attached to the third connecting line, and a relief valve attached to the third connecting line between the vacuum regulator and the filter.

Aspects may further include a fourth connecting line extending from the third connecting line between the relief valve and the filter, a port connected to the fourth connecting line, a fluid trap connected to the fourth connecting line between the port and the filter, and a third check valve connected to the fourth connecting line between the port and the fluid trap.

Alternatively, aspects may include a fourth connecting line extending from the first connecting line between the suction source opening and the first check valve, a port connected to the fourth connecting line, a fluid trap connected to the fourth connecting line between the port and the first connecting line, and a third check valve connected to the fourth connecting line between the port and the fluid trap.

Aspects may further include an exhaust line extending from the suction source and a muffler attached to the exhaust line. The piston check valve may have a cracking pressure of at least 0.29 psi. The first check valve may have a cracking pressure of at least 0.5 psi. The cracking pressure of the piston check valve may be greater than 2.5 psi. The cracking pressure of the first check valve may be greater than 3.5 psi.

Aspects may further include a fluid collection system, having a disposable collection container having a flexible liner, a receiving housing sized to receive the disposable collection container, the receiving housing including a cavity, a piston assembly positioned within the cavity, the piston including a piston check valve, a suction source connectable to the disposable collection container, a filter positioned between the suction source and the cavity, a first connecting line extending between a suction source opening, configured to communicate the suction source to the disposable collection container, and the filter, and a first check valve connected to the first connecting line between the suction source opening and the filter.

Additional objects and advantages of aspects will be set forth in part in the description which follows, and in part will be obvious from the description, or may be learned by practice thereof. Such objects and advantages may be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE FIGURES

A better understanding will be had upon reference to the following description in conjunction with the accompanying drawings in which like reference numerals represent like parts.

FIG. 1 is a perspective view of a liquid collection system, in accordance with exemplary aspects.

FIGS. 2-4 are perspective views of a disposable liquid collection container in accordance with exemplary aspects.

FIGS. 26-28 illustrate an exemplary filter, in accordance with exemplary aspects.

DETAILED DESCRIPTION

Figure 5:
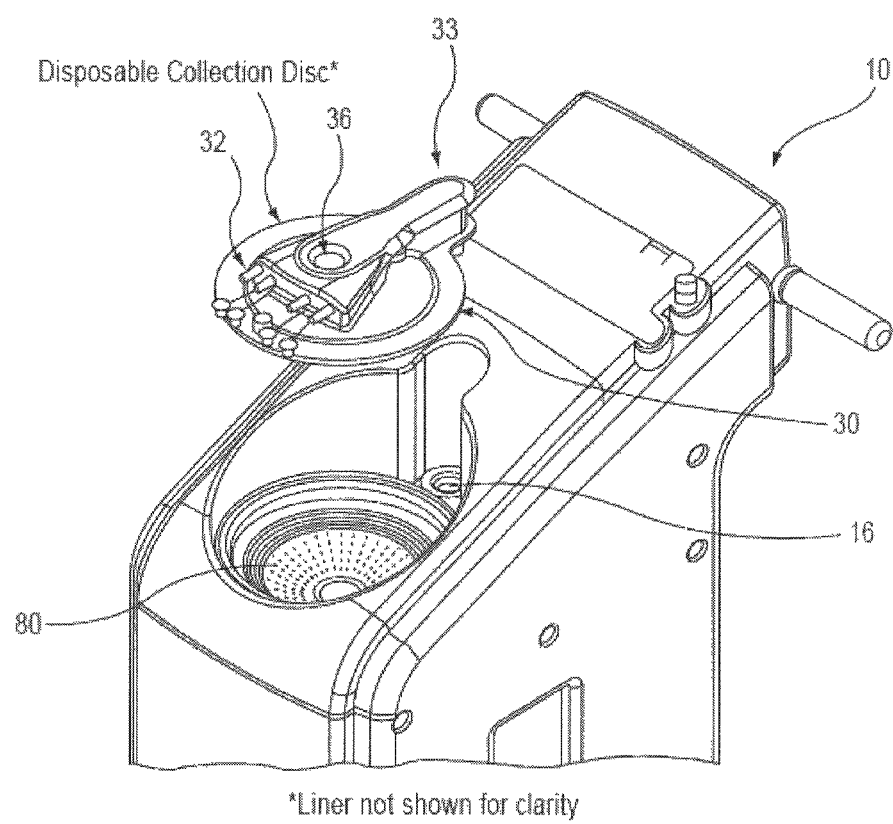
FIG. 5 is a perspective view of a liquid collection system, illustrating exemplary components.
Figure 6:
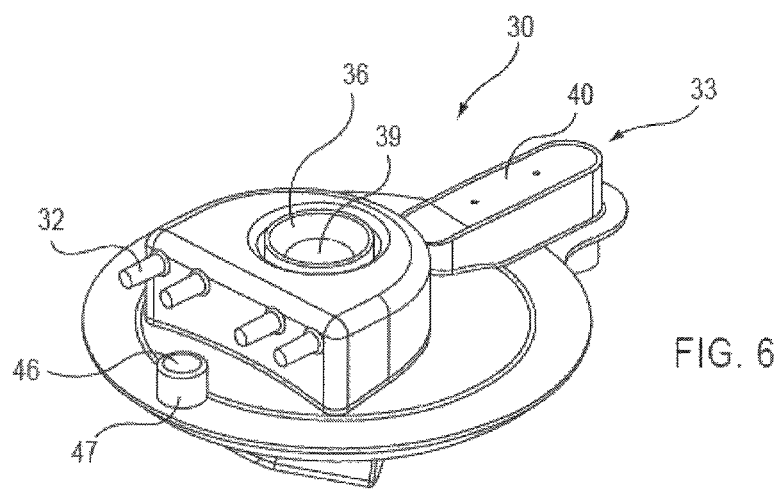
FIGS. 6-11 are perspective views of a lid for a disposable liquid collection container, in accordance with exemplary aspects.
Figure 7:
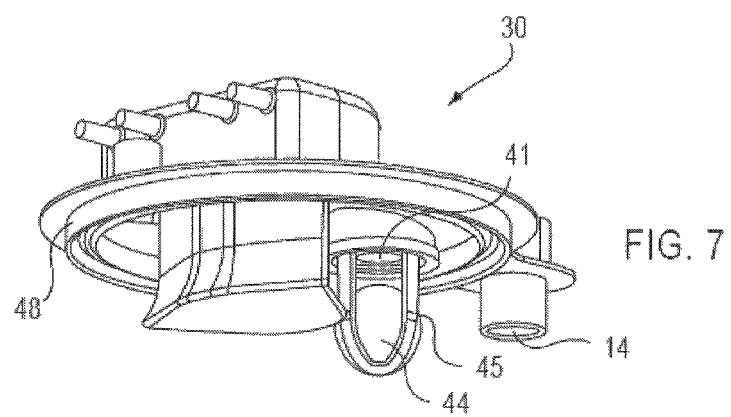
Figure 8:
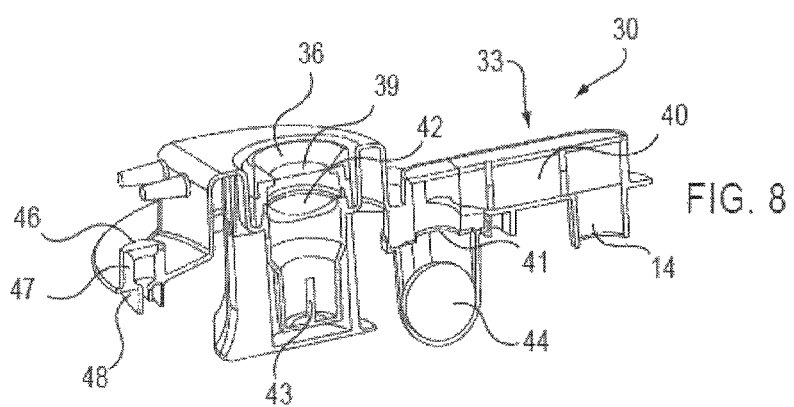
Figure 9:
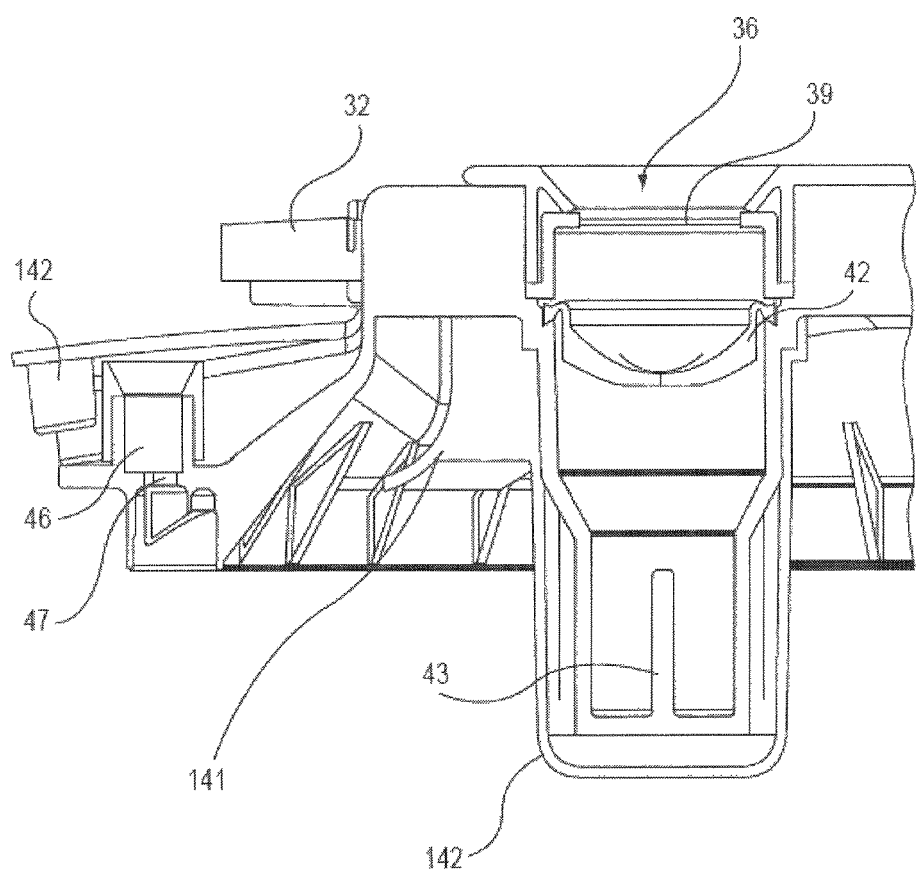
Figure 10:
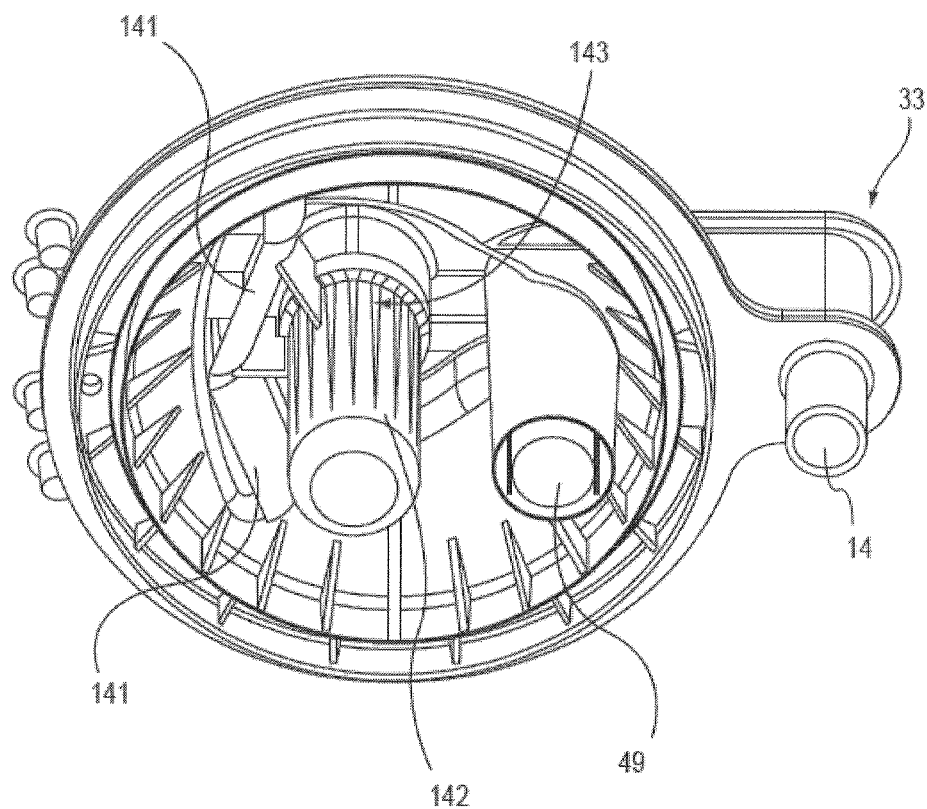
Figure 11:
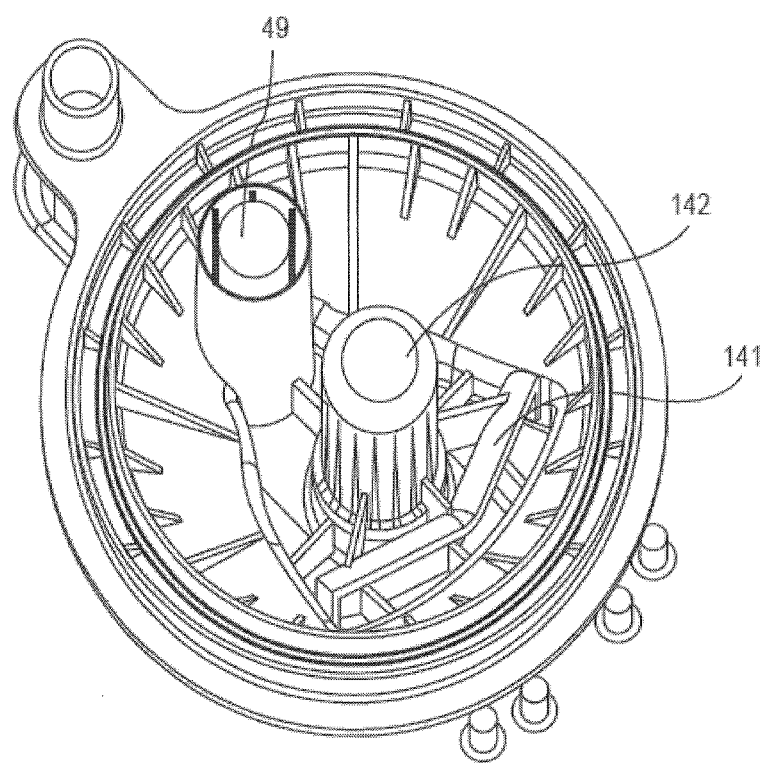

Reference will now be made in detail to aspects, examples of which are illustrated in the accompanying drawings. Wherever possible, the same reference numbers will be used throughout the drawings to refer to the same or like parts.

FIGS. 1-5 show a portable fluid collection system 10 (herein also referred to interchangeably as a liquid collection system), according to exemplary aspects. The portable fluid collection system may include any of the aspects described in co-pending application Ser. No. 12/076,842 filed on Mar. 24, 2008, titled LIQUID COLLECTION AND DISPOSAL SYSTEM AND RELATED METHODS or application Ser. No. 12/076,841 filed on Mar. 24, 2008, titled FLUID COLLECTION AND DISPOSAL SYSTEM HAVING INTERCHANGEABLE COLLECTION AND OTHER FEATURES AND METHODS RELATING THERETO, the entire contents of both of which are incorporated herein by reference The system 10 includes a main body, also interchangeably referred to herein as a container receiving housing 12, defining a cavity 15 for receiving a fluid collection container 30 (also herein referred to interchangeably as a liquid collection container or a liquid/fluid collection bag) shown in this figure as an exemplary fluid collection bag. The cavity 15 may have various sizes and shapes. A piston 80 (illustrated in FIG. 5) is located in the cavity 15. The system 10 may also include a handle 14 and wheels 19 to facilitate transport of the system 10. The main body 12 may also include a container holder 18 for receiving a back-up storage container, such as a suction canister.

The term "liquid," as used herein, does not merely refer to a state of matter as defined in the thermodynamic and/or fluid mechanics art. Instead, the term "liquid" also includes any solid particles or gases that may incidentally flow with a liquid medium (e.g., irrigation fluid or blood) or that may be intentionally collected using a liquid medium. For example, when the fluid collection system 10 is used in a surgical procedure, the term "liquid" may refer to a combination of liquid medium (e.g., irrigation fluid, blood, and other bodily liquid from the patient) and any solid particles including, but not limited to, resected tissue removed from the patient's body or harmful particles mixed with smoke or other particulates and/or gases such as may occur in connection with laser, cauterization, and/or other medical procedures. The term "fluid," as used herein may also refer to a liquid medium, solid particles, smoke, gases, particulates, and combinations thereof.

Although not shown in FIG. 1, system 10 may include a vacuum pump for supplying a suction force to the cavity 15 and to the liquid collection bag 30. The system 10 may include appropriate suction conduits (e.g. 14 in FIG. 5) connecting the vacuum pump to the cavity 15 and the liquid collection bag 30. In certain exemplary implementations, instead of, or in addition to, providing the vacuum pump in the main body 12, an alternative suction source may be separately supplied to the system 10. For example, suitable conduits, tubing, fittings, connectors, and/or other hookups may be provided on the main body 12 to allow connection to an external source of vacuum or suction force, such as a wall vacuum in a hospital setting. The availability of an alternative suction source may enable a continuous liquid collection process even when the vacuum pump malfunctions or becomes otherwise unavailable, for example.

The system 10 may include an interface board 13 for enabling control of various features of the system 10. For example, the board 13 may various buttons 56 for controlling the power supplied to the system 10 and for regulating suction power. The interface board 13 may also include one or more visual or audible indicators that provide various information relating to operational characteristics and/or the status of the system 10, for example when the system is ready for operation, whether the storage bag is filled to an indicated level, whether the filter needs to be replaced, and a vacuum level indicator.

The liquid collection bag 30 may be a disposable unit. As shown in FIGS. 2-4, the collection bag 30 may include a lid 31 and a flexible liner 35 attached to or integrally formed with the lid 31, such that the liner 35 and the lid 31 define a substantially sealed interior space therebetween.

The flexible liner 35 may comprise a sufficiently durable, yet collapsible material, so that, upon applying a negative pressure inside the interior space (e.g., during and/or after fluid is removed from the interior space), the liner 35 can collapse into a smaller volume. The term collapse as used herein, includes and is interchangeably referred to herein as actions in which the sides of the liner 35 fall in, cave in, retract, unextend, compress in, fold, or roll, among other things, and/or which may optionally be forced or otherwise collapsed via operation of a scraping or other squeegee type apparatus.

In some exemplary applications, the liner 35 may additionally include one or more support structures that guide the liner 35 to expand/extend and collapse/retract in a predetermined manner. For example, as shown in FIG. 4, the liner 35 may include a plurality of support rings or a spiral shaped support 37 (e.g., ribs or spirals made of flexible wires), spaced apart from one another along the length of the liner 35, so that the liner 35 may expand and collapse in a bellow-like manner. Alternatively, as seen in FIG. 3, the liner 35 may not include such support rings 37. In either case, in variations the liner 35 extends and retracts along its longitudinal axis. Other variations may include other directions in which the liner 35 extends and retracts.

At least the front portion of the main body 12 may comprise a transparent or translucent material that allows visualization of the liquid being collected in the collection bag 30. In some exemplary implementations, the front portion of the main body 12, the liner 35 and/or the cylindrical body may include gradation marks to indicate the amount of liquid being collected in the collection bag 30.

The lid 31 may include one or more collection ports 32 configured to connect to various medical devices that draw liquid into (or extract liquid from) the collection bag 30. The collection ports 32 may have various different sizes and shapes to accommodate various medical devices that may be used with the system 10. The collection ports 32 may be configured to mate with one or more suction instruments or other devices (interchangeably referred to herein as "suction instruments" or "medical devices") by way of suction tubings for the purpose of drawing liquid into the collection bag 30. The collection ports define one or more fluid passageways via which liquid is transported from the individual (or multiple) suction instruments to the interior space of the collection bag 30. Each of the collection ports 32 may be covered. The cover may be provided via a cap, plug, or flap among others, which closes the respective collection port when not in use. The lid 31 may include suitable valves (e.g., duckbill valves, check valves, spring loaded plungers) to prevent, or at least minimize, liquid dripping while the suction instruments and tubings are disconnected from the collection bag 30 and disposed of in a suitable disposal container (e.g., a red bag). Thus, the lid 31 may reduce the risk of the clinicians' exposure to potentially hazardous materials.

In an exemplary implementation, as shown in FIGS. 1-3, the lid 31 may also include a back-up vacuum port 34 for connecting to a back-up storage container in case the collection bag 30 becomes full or inoperable during a liquid collection process. As illustrated in FIG. 4, the lid 31 may also include a discharge port 38 for evacuating the collected liquid from the collection bag 30, such as after a medical procedure is completed. In an alternative variation, the lid 31 may not have any separate discharge port 38. Instead, one or more of the collection ports 32 may be used to empty the collection bag 30.

During use, the liner 35 is extended to receive fluid, as shown in FIG. 3. As will be explained in detail herein, while the collection bag 30 is being emptied, the liner 35 may collapse again into a state that is substantially similar to its original fully-collapsed state. After an acceptable quantity of liquid is removed from the collection bag 30, it may be removed for disposal in its near-collapsed state.

To begin a liquid collection process, the collection bag 30 is positioned, in its collapsed state, on the mouth portion 11 of the cavity 15, as shown in FIG. 1. An unused, collapsed liquid collection bag may include a holding mechanism such as a strap or band that assists in maintaining the liner portion of the collection bag in a suitable collapsed position. Once positioned in place, the lid 31 of the collection bag 30 may sealingly engage the mouth portion 11 of the cavity 15, so as to form a substantially air-tight enclosure inside the cavity 15 and exterior to the collection bag 30.

FIGS. 6-11 illustrate exemplary aspects of lids for a disposable fluid collection container. In FIGS. 6-11, the lid 30 defines a vacuum passageway 40 having a U-shaped configuration. The first end 41 communicates with an interior space of the collection bag, and the second end 14 communicates with a vacuum source 16 (in FIG. 5) so as to supply suction force to the interior space of the collection bag. Near the first end 41 of the vacuum passageway 40, the lid 30 includes an overflow valve having a floating ball 44 housed in a cage-like structure 45. Other exemplary lids 30 may include a hydrophilic valve 49 (in FIG. 1-11), such as a porous plastic valve (PPV). As the liquid level in the collection bag 35 reaches the elevational position of the valve, the floating check valve 44, 45 rises to close the vacuum passageway 40 thereby preventing the liquid from flowing into the vacuum pump or the hydrophobic valve 49 blocks the pores of a hydrophobic material, for example using surface tension, and thereby prevents liquid from flowing past the material.

The lids illustrated in FIGS. 4-11 differ from the lids 31 depicted in FIGS. 1-3, in that, among other things, they include a breakable closure member, 39 (in FIG. 9) (e.g., a foil, plastic film, rubber) for closing an evacuation port 36 of the lid. The opening may also include a two-way check valve 42, and a pin 43, for example. FIGS. 5-11 show a variation of the lid in which the exterior of the passageway 40 providing communication between the liquid collection bag 30 and the suction source 14 is configured as a gripping member 33 on the exterior of the disposable lid. This gripping member 33 provides an area removed from the collection ports 32 and from the disposal port 36 by which a user can grip the disposable lid to attach and remove the disposable lid.

Unlike the collection ports 32 shown in FIG. 1-3, which are used to both collect and remove liquid for the collection bag 30, the evacuation ports, 38 of FIGS. 4-5 and 36 of FIGS. 6-11 are not used during liquid collection operation and remain sealed by the closure member 39 until the collection bag is to be emptied.

The lid 30 of FIGS. 5-11 also differs from the lids of FIGS. 1-4, in that it forms an interstitial opening 47 for supplying a source of suction pressure to a space between the rigid receptacle defining a cavity and the collection bag during an evacuation process. The source of suction pressure may be used to equalize the pressures inside and outside of the collection bag during an evacuation process, so that the collection bag may substantially maintain its normal shape during that process. The interstitial opening 47, like the evacuation port 36, may be closed off during the liquid collection process by a breakable closure member 46. Use of the interstitial opening will be explained in further detail in connection with FIGS. 12 and 17.

The lid may include a shelf 141 located between the interior opening of the plurality of ports and the opening communicating with the vacuum source. The shelf 141 extends a sufficient distance to divert collected fluids away from the vacuum source. The shelf may be shaped to direct entering fluid toward the liner walls and away from the shut off valve. The lid may also include a screen 142 surrounding the opening to the evacuation opening. The screen may be shaped to prevent solids collected in the fluid from exiting the collection container during disposal.

The shelf 141 and the screen 142 may also be shaped to prevent the liner from collapsing against the opening to the evacuation port 36, which could, without the present configuration, close off the evacuation port before the contents of the liner are fully evacuated. For example, during evacuation of the contents in the disposable liquid collection container 30, the contents are evacuated via suction through the evacuation port 36. The liner collapses and is drawn toward the evacuation port during this process. If the liner blocks the openings in the screen before all of the contents are removed, the disposal system would be unable to remove the remaining contents. In an aspect, the shelf 141 may be shaped and placed in relation to the screen 152 in a manner that prevents the liner 35 from blocking all of the openings in the screen. For example, the shelf 141 may comprise a portion that extends from the surface of the lid adjacent the screen 142 in order to maintain fluid communication between the evacuation port and the distal portion of the liquid collection container. Thus, at least a partial opening is maintained to the evacuation port, at least in the area between the shelf 141 and the screen 142 to allow continued evacuation of the contents through the openings 143 in the screen 142 and out the evacuation port 36.

Liquid Collection and Disposal Sequence

Figure 12E:
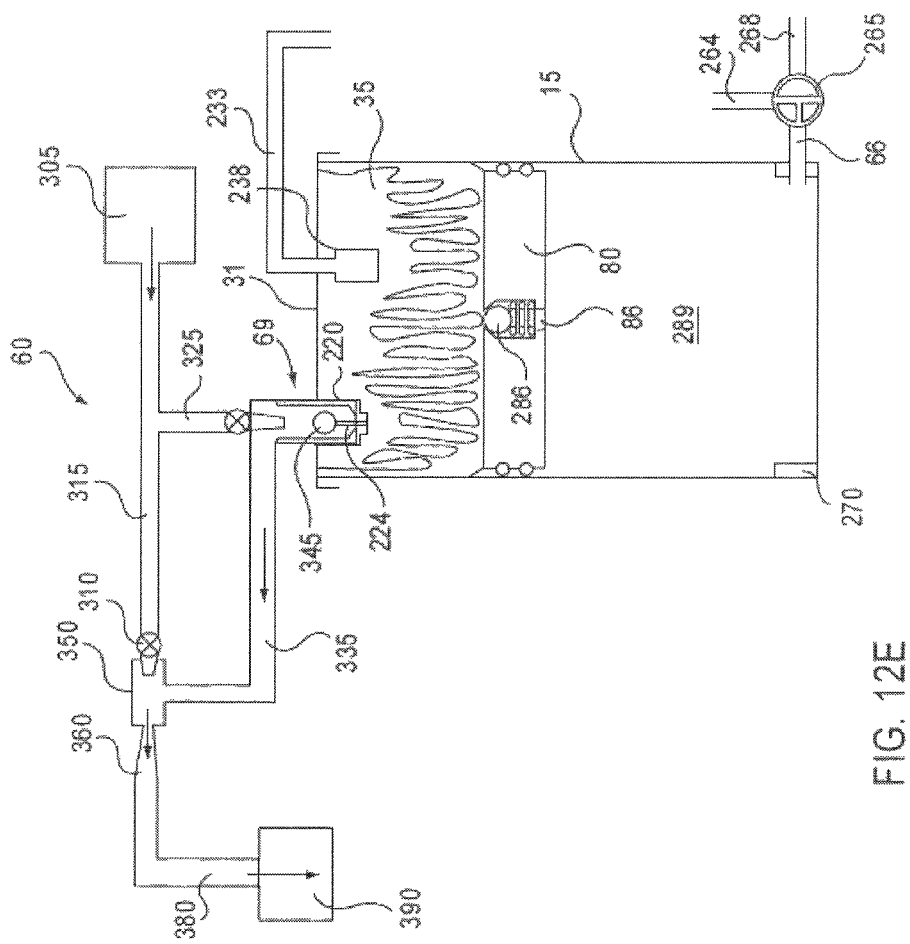
FIGS. 12-13 are schematic illustrations of a liquid collection and disposal sequence, in accordance with exemplary aspects.
Figure 13:
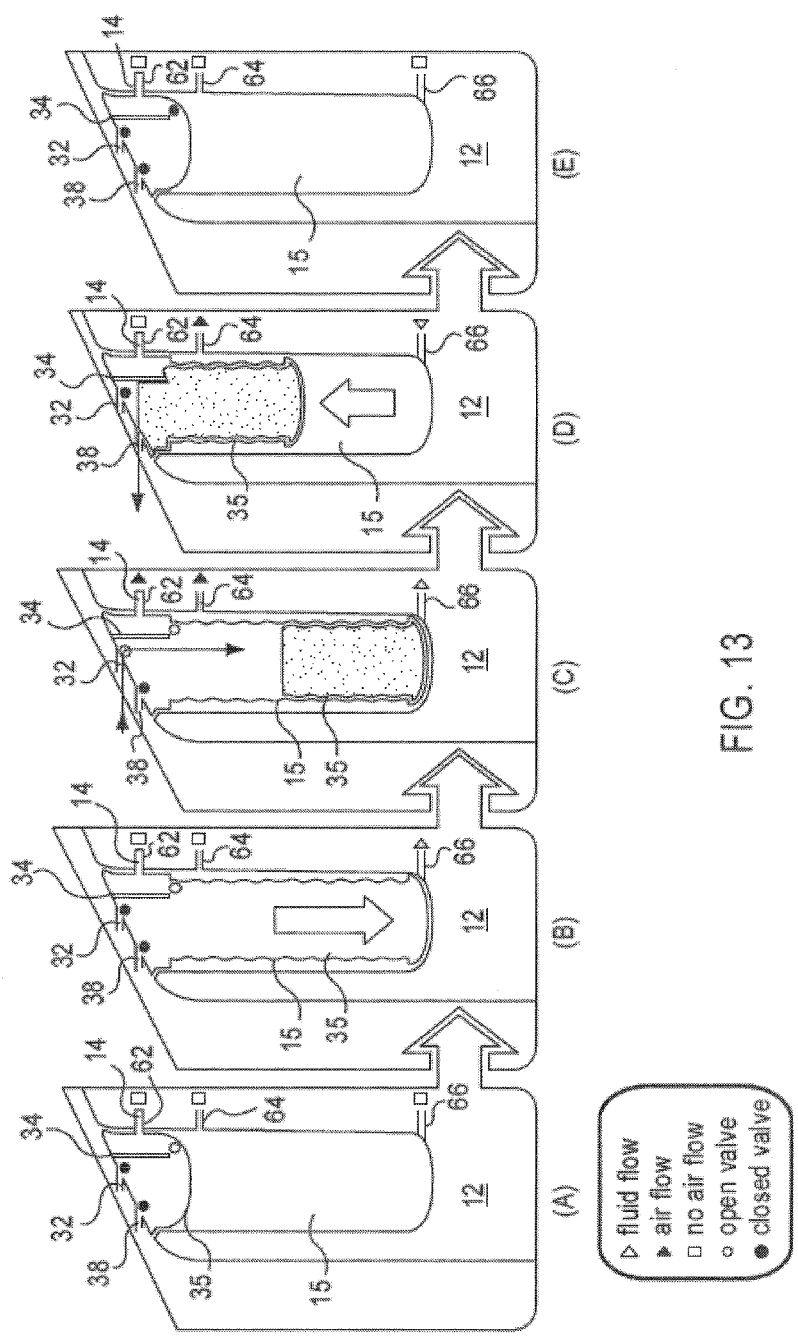

FIGS. 12 and 13 illustrate exemplary aspects of a liquid collection and disposal sequence. As shown in FIG. 12, the system includes a liquid collection bag 30 and a rigid container 15 configured to receive the collection bag 30. The collection bag 30 may include a lid 31 and a collapsible liner 35 attached to the inner surface of the lid 31 to form a substantially sealed interior space therebetween. When the collection bag 30 is placed on the top of the rigid container 15, the lid 31 may substantially seal the opening of the container 15.

As shown in FIG. 12, the collection bag 30 may include a suction conduit 233 for connecting the interior space of the collection bag 30 to a suitable suction source (e.g., vacuum pump). The lid 31 may define an access port 220 normally closed by a flexible valve 226, such as an elastic slit valve that is deflected to open the access port 220. The access port 220 may be configured to receive a hose junction 240 and/or an evacuation connector 66. The lid may also define a second opening that will provide a connection to an evacuation connector.

The container 15 may include a piston 80 (much like a syringe) slidably positioned inside the container 15 to separate the internal space of the container 15 into an upper space 281 and a lower space 289. Aspects of the piston will be described in more detail below. The container 15 may also include a stopper 270 near its bottom, to prevent the piston 80 from descending below the level of the first connection 262. As shown in position 12A, the piston 80 may be initially positioned near the top of the container 15 to receive the collection bag 30.

FIG. 13 illustrates that cavity 15 may include three vacuum connectors: a first connector 62, a second connector 64, and a third connector 66, each of which may be connected to a vacuum pump. When the collection bag 30 is placed in the cavity 15, the vacuum port 14 of the lid 31 may automatically connect to the first connector 62, so as to supply suction force to the interior space of the collection bag 30. This suction force, in turn, is communicated to the collection ports 32. Each of the vacuum connectors 62, 64, 66 may include a suitable valve to selectively open and close communication with the vacuum pump or to an alternate source of vacuum pressure. In some exemplary variations, the valve associated with the third connector 66 may comprise a three-way valve that can selectively establish fluid communication between the cavity 15 (exterior to the bag 30) and atmosphere.

The collection bag 30 may also include various valves associated with the collection ports 32 and the discharge port 38. These valves associated with the collection ports 32, discharge port 38, and vacuum port 14 are schematically shown in FIG. 13 with circles adjacent the corresponding ports. Solid circles represent closed valves, and open circles represent open valves.

In FIG. 12, the optional three-way valve 265 may be rotated to align the first connection 62 with the a suction source 268 to communicate such pressure within the lower space 289. The suction pressure applied to the lower space 289 draws the piston 80 down into the container 15, which in turn draws the liner 235 into the cavity, thereby expanding the liner into the cavity, as shown position 12C and 13B. Although position 13B illustrates the valves associated with the collection ports 32 to be closed, at least one of the valves associated with the collection ports 32 or the discharge ports 38 may be opened to allow air to flow into the collection bag 30. This action draws the liner 35 into the cavity 15 without distorting the shape of the bag and facilitates the downward movement of the piston 80 The suction force applied to the lower space 289 may be greater than the opening pressure of a check valve 86 in the piston 80, so as to open a throughhole 284 and evacuate any excess air in the upper space 281, which may enhance the seal between the lid 31 and the container 15.

However, it may be preferred for the check valve 86 to remain in a closed position during downward movement of the piston 80, so as to further enhance the pressure differential between the lower space 289 and the upper space 281, thereby further facilitating the downward movement of the piston 80 within the cavity.

In an alternative implementation, the liner 35 may not be drawn into the bottom portion of the cavity 15 prior to receiving the liquid. Instead, as the liquid is being collected, the weight of the liquid may cause the liner 35 to expand into the cavity 15.

The second connector 64 provides a connection to the interstitial area between the outside of the line 35 and the inner wall of the cavity 15. Although the second connector 64 is shown in the figures to be located at a position vertically below the lowermost end of the collection bag 30, as shown in FIG. 13, it will be apparent to one of ordinary skill in the art that the second connector 64 may selectively not be opened to atmosphere until the lowermost end of the collection bag 30 is positioned vertically below the elevational position of the second connector 64.

Thereafter, liquid may be drawn into the collection bag 230, as shown in position 12C and 13C. Communication with a first connector 62 may be opened so as to supply suction force into the interior space of the collection bag 30, and, in turn, via the collection bag 30 to the collection ports 32. During the liquid collection process, the second connector 64 may opened to counterbalance the vacuum force applied to the interior space of the collection bag 30 so that the liner 35 may substantially maintain its normal shape. That is, the second connector opens to a suction force thereby preventing the liner 35 from being drawn back up towards the lid 31 under the influence of the negative pressure within the interior space of the collection bag 30.

Alternatively, a continuously applied suction force in the lower space 289 may cause a check valve 86 in the piston to open, so as to communicate the suction pressure with the upper space 281, which may counterbalance the suction force applied inside the interior space of the collection bag 230 to prevent or reduce collapse or deformation of the liner 235 during the liquid collection process.

The liquid collection process may thereafter end because the medical procedure is completed, for example. This action may also end as a result of suction pressure shutoff, which may occur, for example, when the liquid level rises to the level of the shutoff device 238. For example, when the liquid level reaches the level of the shutoff device 238, the shutoff device 238 may automatically shut off the conduit 233 to stop the liquid collection process, as shown in position D.

When the collection bag is full and/or otherwise needs to be emptied, the collection system 10 may be transported to a disposal station to extract the collected liquid from the collection bag 30, as illustrated in positions 12E and 13D. The disposal connector 69 may include a drip-free connector valve 345, which is biased to close the distal end of the disposal connector 69. Inserting the disposal connector 69 may cause the connector valve 345 to open, so as to establish fluid communication between the access port 220 and the eductor 350. The disposal connector 69 may also pierce a closure over an evacuator opening in the lid 31. Once the valve associated with the discharge port is opened and connected to a disposal station 60, and the collected contents of the collection bag 30 are evacuated.

The operation of the disposal station will be described in more detail in connection with FIG. 17. FIG. 12E illustrates that the disposal station may include an eductor 350 positioned between a source of water or other rinse fluid 305 and a sanitary sewer 390 to create a pumping force sufficient to draw liquid out of the collection bag 230. In addition, a venturi 360 may be suitably positioned, (e.g., adjacent the eductor 350 in the discharge conduit 380) so as to create a greater pumping force.

To control the collapse geometry of the liner 35 in a manner that does not occlude and prevent the desired discharge liquid flow, check valve 86 may be set in a closed position. The closed position of the check valve 86 prevents air from flowing into the space between the liner 35 and the container 15. Because of the relatively limited air in the space outside of the liner 35, the walls of the liner 35 will not be pulled away from the walls of container 15 and therefore will not close off the passage of liquid within the liner 35.

At this stage, the optional three-way valve 265 may be aligned to communicate the lower space 289 with atmosphere via the first connection 62 and a fourth connection 264, as shown in position E. This selection allows the pressure inside the lower space 289 to reach atmospheric pressure during the evacuation process, so as not to interfere with the collapse of the liner 235.

Maintaining the pressure inside the cavity at atmospheric pressure may provide a sufficient pressure difference between the cavity 15 and the interior space of the collection bag, such that the liner 35 may collapse itself toward the lid 31 as the collected liquid is drawn out of the collection bag 30.

For example, maintaining the pressure in the lower space 289 at atmospheric pressure allows the piston 80 to rise during the evacuation process, due to a differential pressure between the upper space 281 (which is subject to a suction pressure) and the lower space 289 (which is open to atmosphere). Because the piston 80 moves up as the liner 35 collapses, the collapse of the liner 35 takes place primarily near the piston 80, and occlusion of the sidewalls of the liner 35 during the evacuation process may be effectively prevented.

Second connector 64 illustrated in FIG. 13 may be open to vacuum pressure or may be closed off entirely, so as to provide selective regulation of air pressure within the cavity 15 exterior to the collection bag.

Once an acceptable quantity of the liquid is removed from the collection bag 30, and the collection bag 30 is collapsed, the discharge connector 69 is removed from the access port 220. For practical purposes, it may be sufficient for the liner 35 to compact itself enough so as to make subsequent handling and disposal thereof more efficient. After the collected liquid is substantially removed from the collection bag 30, the valves associated with the collection ports 32, the discharge port 38, and the overflow valve are closed sufficiently to inhibit air from flowing into the interior space of the collection bag 30. Minimizing the amount of air flow into the collection bag 30 allows the collection bag 30 to remain in a substantially collapsed state for disposal. That is, large quantities of air will not be allowed to leak back into the interior space of the bag 30 once the vacuum pressure is removed therefrom.

The collection bag 30 is then removed from the container 15 and placed in a red bag for disposal, for example. A new collection bag may be placed onto the container 15 for the next series of medical procedures.

Disposal Station

Figure 14:
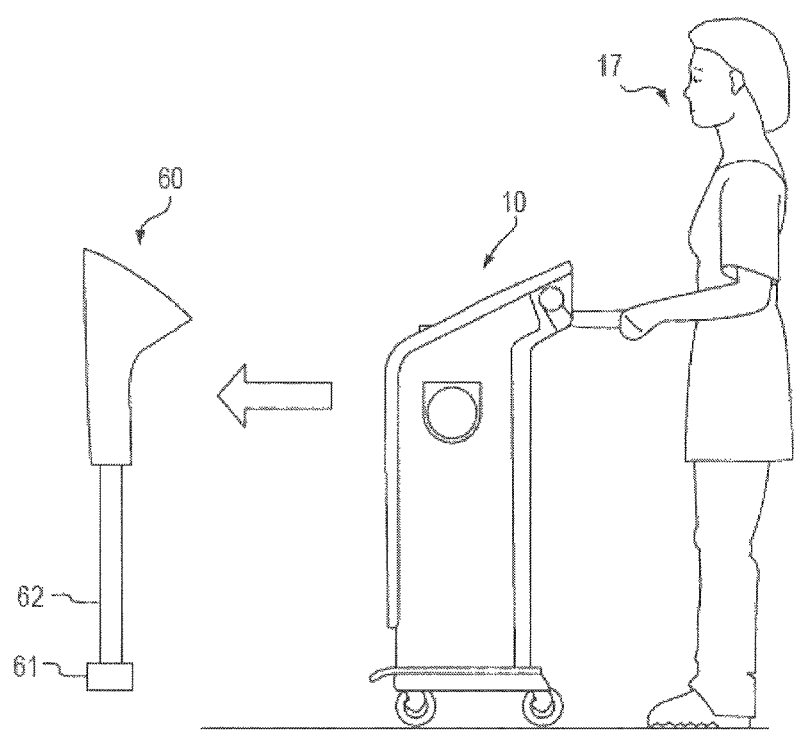
FIG. 14 is a schematic illustration of a liquid disposal process, in accordance with exemplary aspects.

Once the collection bag 30 is full or otherwise needs to be emptied, the portable liquid collection system 10 may be transported to a disposal station by, for example a clinician 17 to evacuate the collected liquid from the collection bag 30, as shown in FIG. 14. Although evacuation of the collection bag 30 is not necessary for disposal thereof (e.g., a filled collection bag 30 may be disposed of with liquid still present within the interior space thereof), one aspect may allow for the evacuation of the collection bag 30 to reduce the volume of red-bag waste produced by disposal thereof.

Figure 16:
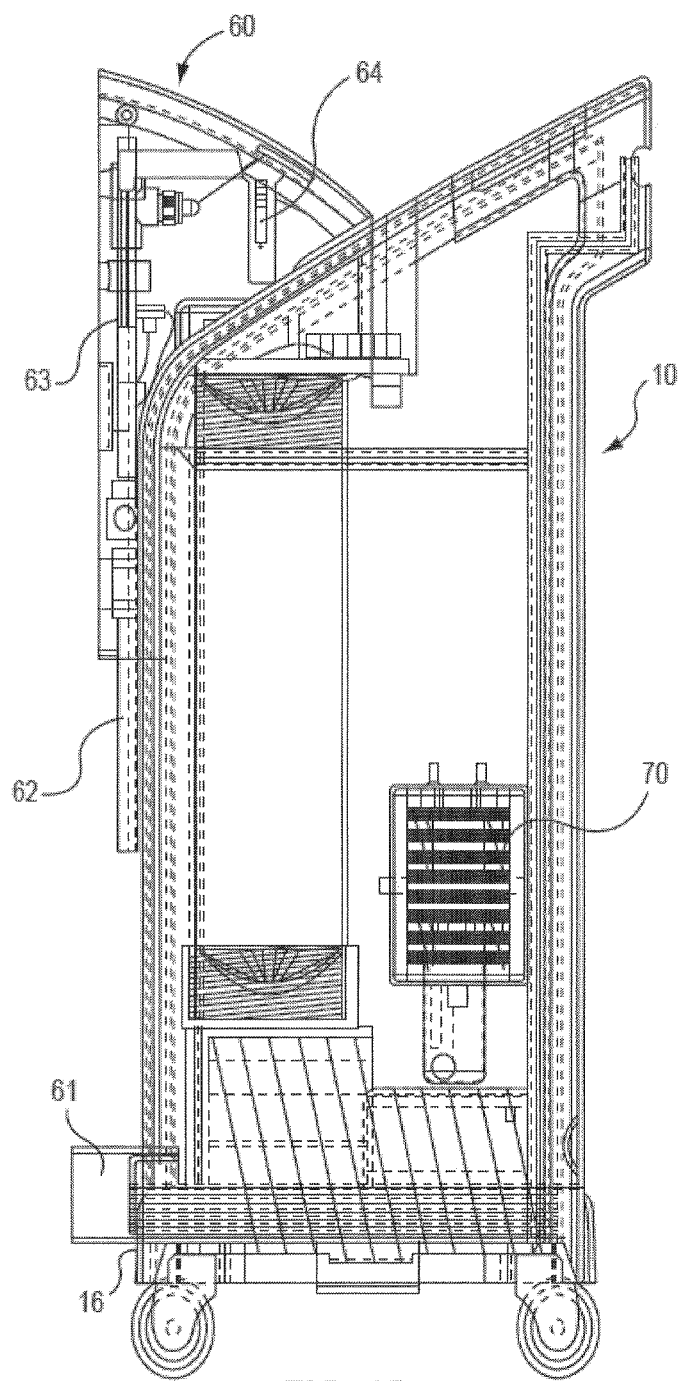
FIG. 16 is a see-through view of a liquid collection and disposal system, in accordance with exemplary aspects.

In some exemplary variations, the disposal station may comprise a docking station 60 having a fluid connector configured to automatically (or manually) connect to the discharge/evacuation port 38, 36 (for the implementation shown in FIG. 4, 5), the inlet port 32 (for the variations shown in FIGS. 1-3). FIG. 16 illustrates an exemplary portable liquid collection system docked at a disposal station 60.

Figure 15:
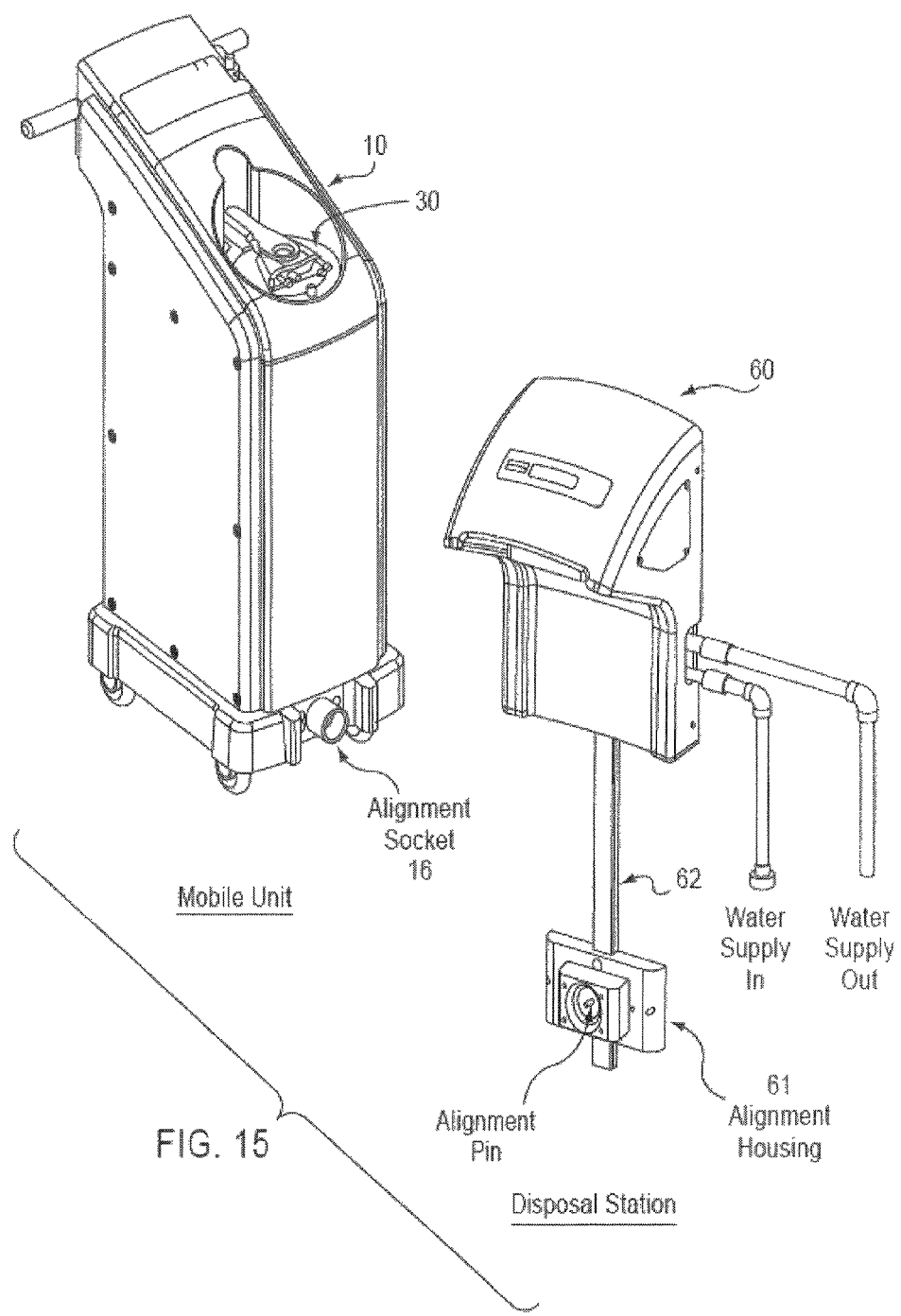
FIG. 15 is a view of another exemplary liquid collection and disposal system, in accordance with exemplary aspects.

FIGS. 14 and 15 illustrates that the disposal station 60 may include a reference structure 62 and a latching member 61 fixed to the reference structure 62 for engaging a corresponding latching member 182 of the liquid collection system 10. Among other things, this approach allows the liquid collection system 10 to be securely and accurately positioned at a predetermined location relative to the disposal station 60. The disposal station may include a connection to a fluid supply, such as water, and a connection to a disposal supply through which collected liquid is evacuated and disposed.

The disposal station may be attached to a fixed location, such as to a wall. Alternatively, the disposal station may be mobile.

Figure 17:
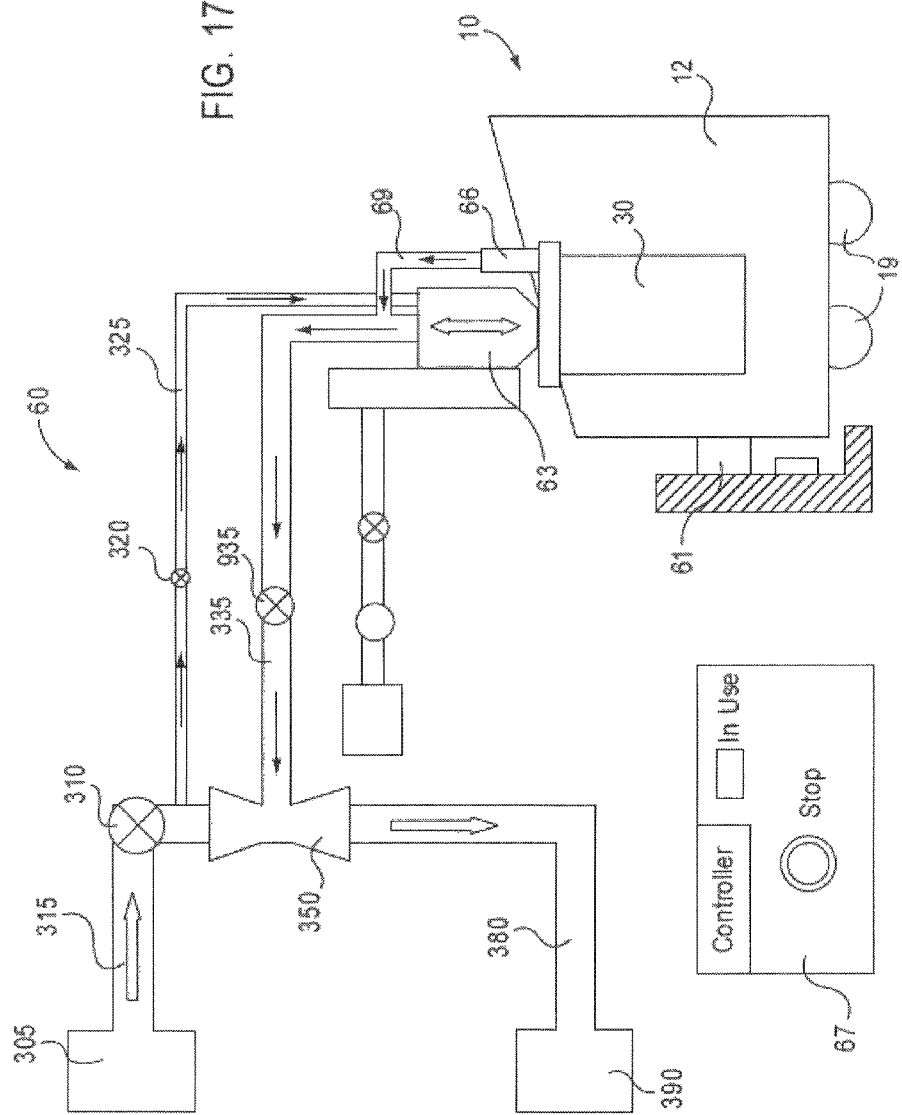
FIG. 17 is a schematic diagram of a liquid disposal station, illustrating various components and their operational characteristics associated with a liquid collection system, in accordance with exemplary aspects.
Figure 18:
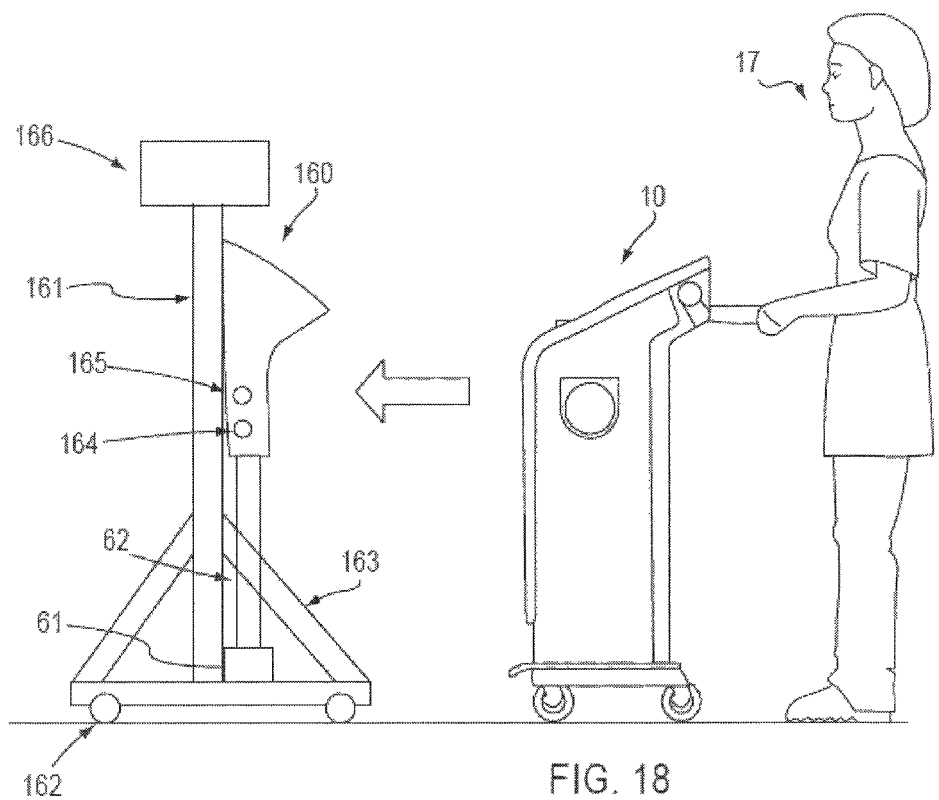
FIG. 18 is a perspective view of a disposal station, in accordance with exemplary aspects of the present invention.

FIG. 18 illustrates a mobile disposal station. The mobile disposal station 160 is attached to a mobile frame 161. As illustrated in FIG. 18, the frame may include a relatively low friction component 162 that allows the station to be moved, such as wheels, rollers, skid plates, tracks, etc. The frame 161 may include front and/or rear supports 163. The mobile disposal station has features similar to those discussed in connection with the disposal station of FIGS. 12-17.

The mobile disposal station includes a connection for receiving a water supply line 164 and a connection for receiving a disposal line 165. The mobile disposal station may include a cord for attaching the disposal station to a power supply.

The mobile station may further include an optional backflow preventer. The backflow preventer may be attached to the mobile frame and connected in series with the water source in order to prevent waste water from flowing back into the clean water supply. For example, the backflow preventer may comprise a one-way valve. Thus, in an aspect, the line of clean water would connect to the backflow preventer 166 and then the backflow preventer 166 would be connected to opening 164 for receiving clean water into the disposal station 160.

To evacuate the collected liquid from the collection bag 30 in some exemplary implementations, the docking station 60 may utilize an eductor of the type described in U.S. Patent Application Publication No. 2005/0183780, entitled "Method and Apparatus for the Disposal of Waste Fluids" and published on Aug. 25, 2005, the entire disclosure of which is incorporated herein by reference. Alternatively or additionally, the disposal station may include a movable connector (not shown) that can be manually connected to the collection bag 30, 130 to evacuate the collected liquid therefrom.

FIG. 17 is a schematic diagram of a liquid disposal station 60, illustrating various components and their operational characteristics associated with a liquid collection system 10.

FIG. 17 illustrates that the liquid disposal station 60 may include a user interface 67 for controlling the disposal station 60.

In certain exemplary variations, the process for evacuating liquid from the liquid collection system 10 may be automatically initiated upon engagement of the latching member, although the system may be configured such that an operator is required to manually initiate the evacuation process after the system 10 has been operatively engaged with the disposal station 60.

A liquid collection system 10 is securely positioned in the disposal station, such as via a latch 61. An evacuation interface 64 and an optional interstitial interface 66 may align with the evacuation port 36 and an interstitial port 47, respectively, of the liquid collection system 10, as shown in FIGS. 6-11. The evacuation interface 63 and the interstitial interface 69 may be connected to a suitable draining system 65 for evacuating the liquid from the liquid collection system.

In some exemplary variations, the draining system for the disposal station may include an eductor 350 that provides a source of suction pressure sufficient to draw the collected liquid out of the collection bag of a liquid collection bag 30. In addition to the eductor, other vacuum sources may be used to draw the fluid out of the collection bag. The eductor 350 and the associated flow connections for evacuating the collected liquid may operate similarly to those illustrated in FIGS. 12-13, for example.

The eductor 350 may be positioned between a source of water or other rinse fluid 305 and a sanitary sewer 390, via a water conduit 315 and a discharge conduit 380, respectively. Rinse fluid may consist of water, another wash fluid (e.g. a detergent or other fluid), or a mixture of water and another wash fluid. As noted above, the term "fluid" may refer to a combination of a liquid medium along with solid particles, gases and/or particulates. The water conduit 315 may include a water valve 310, which may be controlled manually or by other control, such as electric switch. The disposal connector 66 may be then connected to the eductor 350 via an evacuation conduit 335.

Opening the water valve 310 causes the water from the source of water 305 to flow into the eductor 350 to create a pumping force in the eductor 350. This pumping force causes the liner 35 to collapse and then liquid collected in the collection bag 30 to flow into the eductor 350 and then into the sanitary sewer 390 via the discharge conduit 380.

The disposal station 60 may include a pipe conduit 325 that branches from the water conduit 315 to supply cleaning water or other cleaning substance to the disposal connector or evacuation hose junction 64. The pipe conduit 325 may include a valve 320 (e.g., an electric solenoid valve or a ball valve) that controls the water flow into the interior of the disposal connector 66.

After liquid is removed from a collection bag, clean water or other substance from the pipe conduit 325 may flow into the interior of the evacuation hose junction and around a valve, flushing the entire surface of the valve. This can be cycled on and off one or more times to rinse or flush it off as a preventive maintenance for the evacuation interface. The cleaning operation may be performed before the evacuation interface is removed from the evacuation port so that cleaning substance may flow to the exterior of the evacuation interface and then be suctioned back through the interior of the evacuation interface, thereby flushing any residual fluid or other particles from the components of the interior of the interface.

According to one aspect, conduit 325 (which supplies cleaning water to the disposal connector 66) is in fluid communication with discharge conduit 380, which is used to "charge" the eductor 350, and to thereby suction fluid from the collection bag 30 (as described above). In this manner, cleaning fluid will not be supplied to the disposal connection 66 unless the eductor is suctioning fluid from the collection bag 30, thereby preventing unintended flooding of the collection bag 30 with cleaning water.

The interstitial port 47 of the lid 31 may be in fluid communication with an interstitial space within a cavity external to a liquid collection bag, and the supply of a suction force to the interstitial space may equalize the pressure inside and outside of the collection bag during an evacuation process, so that the collection bag may remain substantially uncollapsed during the evacuation process. Providing the interstitial port 47 in the lid 31 may eliminate the need for a power supply in the liquid collection system 10 during the evacuation process, which may otherwise be required to supply suction source to the interstitial space, similarly to the function of the second vacuum connector 64 in FIG. 13.

In other variations, a seal between the lid of the liquid collection bag and the top 11 of cavity 15 and at least seal between the piston and the inner walls of the cavity maintain vacuum pressure on the outside of the collection bag by preventing air from entering the interstitial space so that the sides of the bag do not collapse during an evacuation process. By limiting air flow into the interstitial space between the bag and the inner walls of the cavity, communication between a suction source and the interstitial space is unnecessary/optional during an evacuation process. In addition, air flow into the interstitial space may be controlled via a check valve in the piston. These seals assist in equalizing the pressure inside and outside of the collection bag during a collection process and continue to maintain that pressure up through at least part of an evacuation process.

In exemplary variations, air flow may be allowed into the interstitial space near the end of an evacuation process in order to fully collapse the liquid collection bag 30 by allowing communication between the atmosphere and interstitial space.

According to certain exemplary implementations, the disposal station may include a linear slide, along which the evacuation interface 63 and the interstitial hose junction may slidably engage the evacuation port 36, 38 and the interstitial port 47, respectively. Movement of the evacuation interface 63 and the interstitial interface relative to the linear slide 63 may be controlled, for example, pneumatically by a compressor or other suitable movement mechanism, a flow control pilot, and a flow control valve (e.g., a two-way solenoid valve).

The evacuation port 36, 38 and the interstitial port 47 may remain closed by breakable closure members during the liquid collection process. These breakable closure members may be pierced or broken when the evacuation interface 63 and the interstitial interface 970 engage the evacuation port and the interstitial port.

As shown in FIG. 12, the evacuation interface 63 may include a normally-closed valve (e.g., a duckbill valve, a check valve, a spring-loaded valve, a poppet valve) to open and close its passageway. In the exemplary variation, the valve includes a ball 345 biased against a distal end of the hose junction. The valve may be opened from its normally-closed position by an actuation rod or pin positioned inside the evacuation port, for example.

Piston

Figure 19:
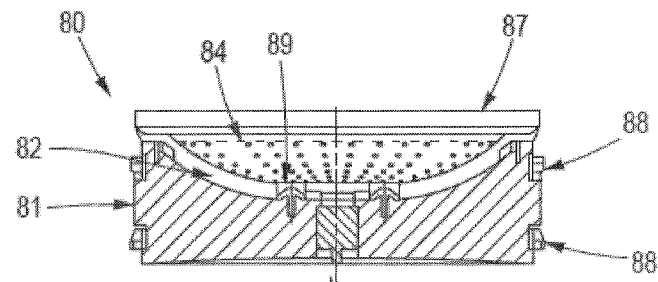
FIGS. 19-21 illustrate an exemplary piston, in accordance with exemplary aspects.
Figure 20:
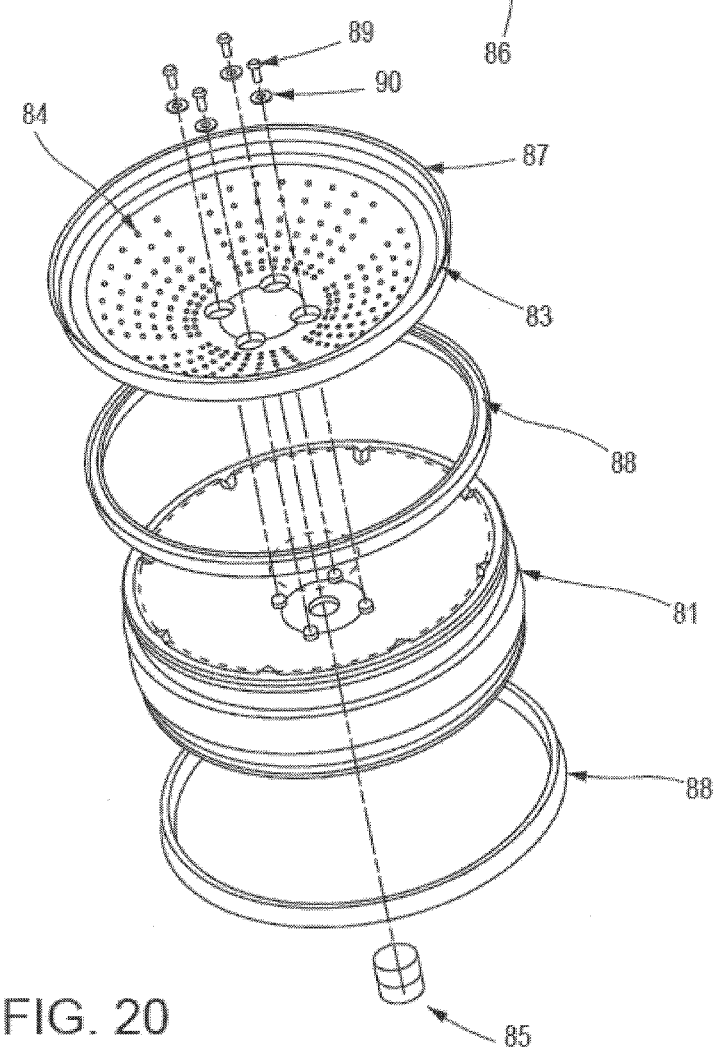
Figure 21:
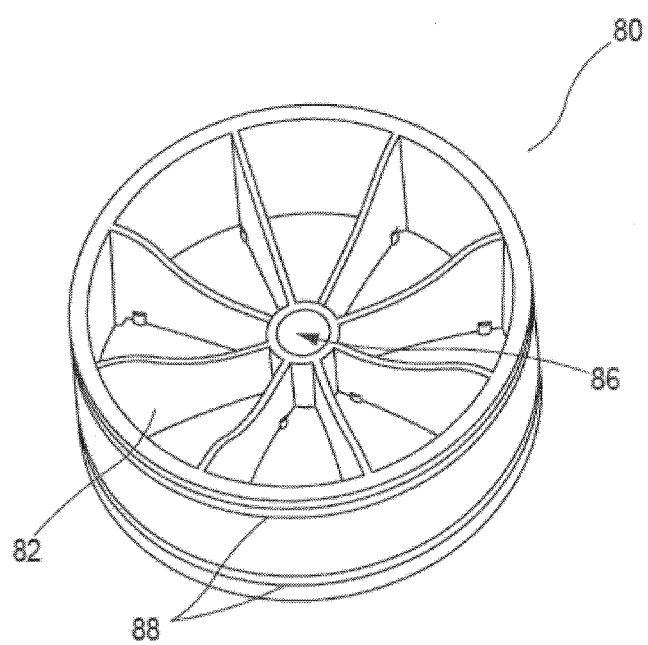

FIGS. 19-21 illustrate an exemplary piston 80. The piston 80 may include a main body 81 shaped to fit a cross section of the interior of the cavity 15 in the liquid collection system 10. In one aspect, the main body may have at least one seal 88 configured to maintain a seal between the piston 80 and the interior wall of the cavity 15. In another aspect, to provide additional sealing capability, the main body 81 may include a plurality of seals 88, such as the two illustrated. Each seal may include, for example, an O-ring attached to the outer peripheral edge of the main body. The O-ring may include a material or be coated with a material to enhance lubricity and/or durability. The piston 80 may also include a though hole 86 and a valve assembly 85, as discussed in connection with FIG. 12.

The piston 80 may also include a scraper ring 83 configured to prevent a liner 35 of a liquid collection bag from being pinched between the inner wall of the cavity 15 and the piston 80. The scraper ring includes a plurality of openings 84 that allow air flow through the scraper ring 83 and an outer peripheral edge 87 that extends above the main body of the piston 80. When inserted into the cavity 15, the peripheral edge 87 of the scraper ring 83 may have a tight, interference fit with the interior wall of the cavity 15. The outer peripheral edge 87 of the scraper ring may be thin so that it does not allow a liner 35 from a liquid collection bag 30 to become caught between the scraper ring and the inner wall of the system. The edge of the scraper ring may also be thin enough that it can be flexed to contact the entire surface area of the inner wall of the cavity 15. As the peripheral edge of the scraper ring is thin, the peripheral edge may also comprise a material that is stiff enough to maintain a tight interference fit and to maintain the shape of the edge as it moves against the cavity wall. Additionally, the peripheral edge of the scraper ring may extend above the main body of the piston to allow a thin edge to maintain compression against the inner cavity wall. This enables the scraper ring to move the bag away from the inner wall of the cavity 15 without catching the bag between the inner cavity wall and the piston.

While the scraper ring 83 has an interference fit with the inner wall of the cavity 15, the scraper ring 83 may be attached to the main body 81 of the piston 80 in a relatively loose manner. For example, the piston assembly may further include a movable connector that connects the scraper ring and the main piston body, wherein the movable connector allows the scraper ring to move with respect to the main piston body. This relatively loose connection with the main body 81 enables the scraper ring 83 to self center against the inner wall of the cavity even when the piston is not centered. The scraper ring may be attached to the main body 81 of the piston, for example, using a bolt such as a shoulder bolt. FIG. 20 illustrates an exemplary variation of the piston 80 having four bolts 89 and four washers 90 attaching the scraper ring to the main body 81 of the piston.

As the piston 80 moves during liquid collection and disposal, the main body of the piston 81 may tip, e.g. become angularly offset, relative to the inner wall of the cavity 15. As the piston becomes cocked, a loose connection between the main body 81 of the piston and the scraper ring 83 allows the scraper ring to maintain its flat position, e.g. angular alignment, and to maintain contact between its outer peripheral edge 87 and the inner wall of the cavity 15. Thus, based on the described configuration, no gap forms between the scraper ring 83 and the inner wall of the cavity such that the liner 35 may be caught.

The scraper ring 83 may include a material having an Ultra High Molecular Weight (UHMW). The molecular weight may be above a million Daltons. The high molecular weight provides a low coefficient of friction and high wear resistance for the scraper ring 83. The lower coefficient of friction causes the scraper ring to have a characteristic similar to significant lubrication. Also, the scraper ring may be formed from a material that is flexible enough to press against the inner wall of the cavity 15 in an interference fit, yet also rigid and stiff. The scraper ring may also include a material that is hydrophobic so that the scraper ring does not swell if it comes in contact with liquid. For example, the scraper ring may comprise a material such as UHMW polyethylene.

The piston may include a support structure to support the surface of the scraper ring 83 adjacent to the main body 81. The support structure may include ribs 82 in at least one of the scraper ring 83, as in FIG. 19, or ribs 82 in the main body 81 of the piston, as in FIG. 21, adjacent to the scraper ring. The ribs 82 may be configured to allow for air flow through the openings 84 in the scraper ring by supporting the scraper ring above the main body 81.

This allows, for example, vacuum pressure from air released through the piston check valve 85 to be distributed across the openings in the scraper ring to the bottom surface of liner 35.

In addition to ribs, the thickness of the scraper ring may be increased in order to provide enough support for the scraper ring to maintain its shape. However, the edge of the scraper ring should be thin enough that it does not allow the liner 35 to be caught between the inner wall of cavity 12 and the edge of the scraper ring 87.

In addition, the scraper ring may be maintained at a flat position, thereby preventing gaps between the inner wall of the cavity 15 and the peripheral edge of the scraper ring 87 even when the scraper ring is firmly attached to the main body 81 of the piston, by increasing the thickness of the main body 81. For example, the thickness of the piston may be increased to about the same amount as the diameter of the piston. Increasing the thickness of the piston 80 prevents the piston from tipping relative to the inner wall of the cavity 15.

Piston Stop Feature

Figure 22:
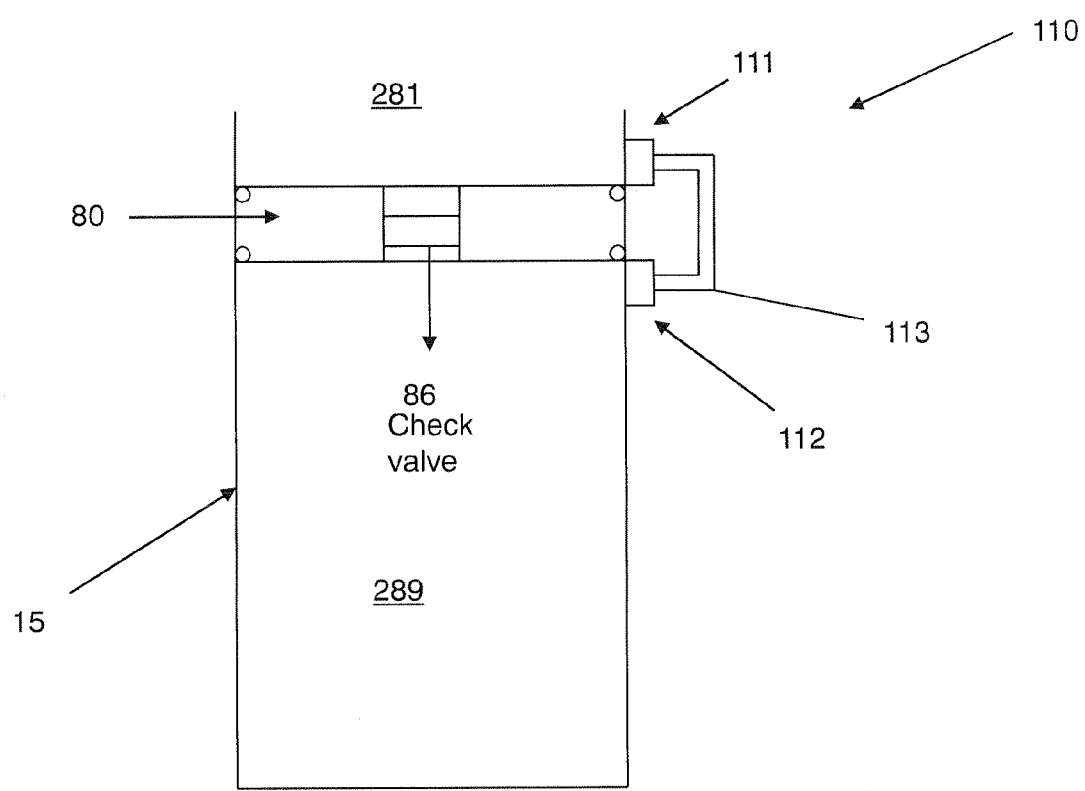
FIGS. 22-25 illustrate an exemplary piston stop feature, in accordance with exemplary aspects.

The collection system 10 may further include a piston stop feature. This may include a stopper on the interior of the cavity 15 that physically stops the piston from rising, similar to the stop 270 illustrated in FIG. 12. Repeated stopping via such a stopper may cause damage to the piston. In addition, the liner 35 may become caught against such a stopper and become pinched between the stopper and the piston 80. In order to prevent such damage, the housing 12 may include a piston stop feature that will function by regulating the pressure between the space above the piston 281 and the space below the piston 289. FIG. 22 illustrates an exemplary piston stop feature.

During an evacuation of collected contents in the liquid disposal bag, there may be a positive pressure under the piston. The portion of the cavity under the piston 289 may be open to the atmosphere, while the upper portion 281 is subject to a lower pressure. Thus, the piston is drawn toward the upper portion of the cavity and assists in the evacuation of the contents of the liquid collection bag. The piston stop 110 communicates the area above the piston 281 with the area below the piston 289 thereby regulating the pressure between them. This stops the movement of the piston because there is no pressure differential between the portions of the cavity on either side of the piston. The piston stop includes an opening 111 to the area above the piston and an opening 112 to the area below the piston. These openings are connected via a channel 113. If the valve is open, movement of the piston 80 will stop. However, if the valve is closed, the piston 80 will continue to move because the pressure difference will not be regulated for the portions of the cavity above 281 and below 289 the piston. The piston stop feature may be configured at any height of the cavity, depending on the desired stopping position of the piston. The piston stop feature may be used to stop the movement of the piston in either direction.

Figure 23:
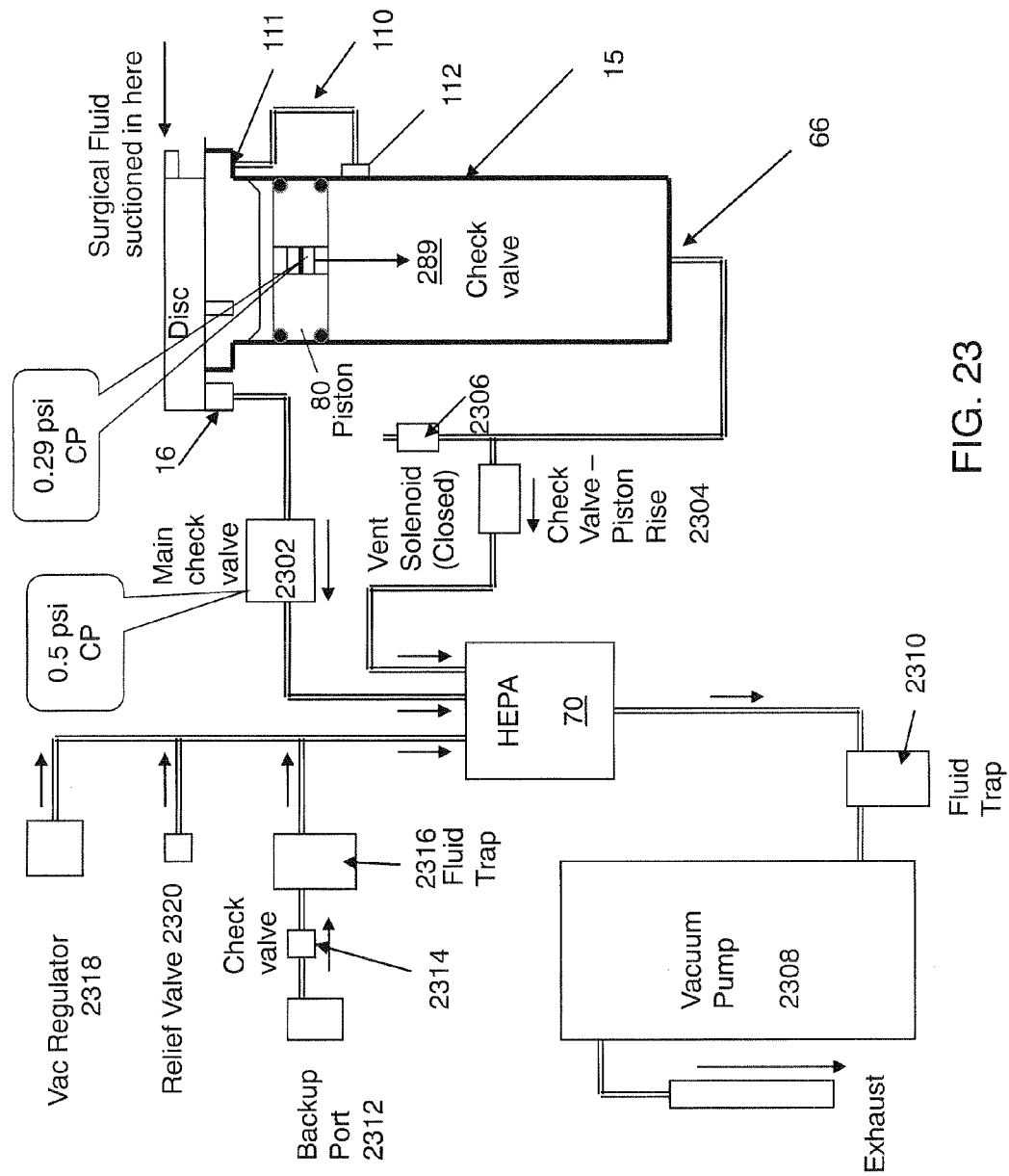
Figure 24B:
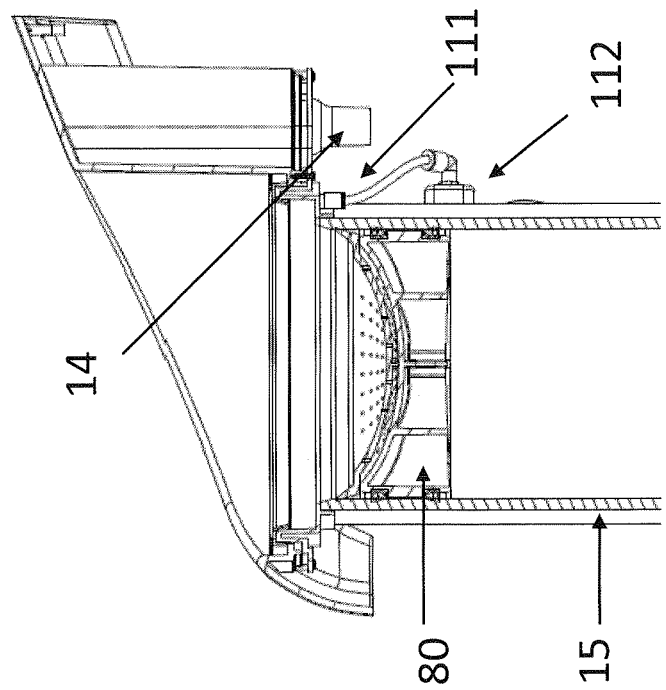
Figure 24A:
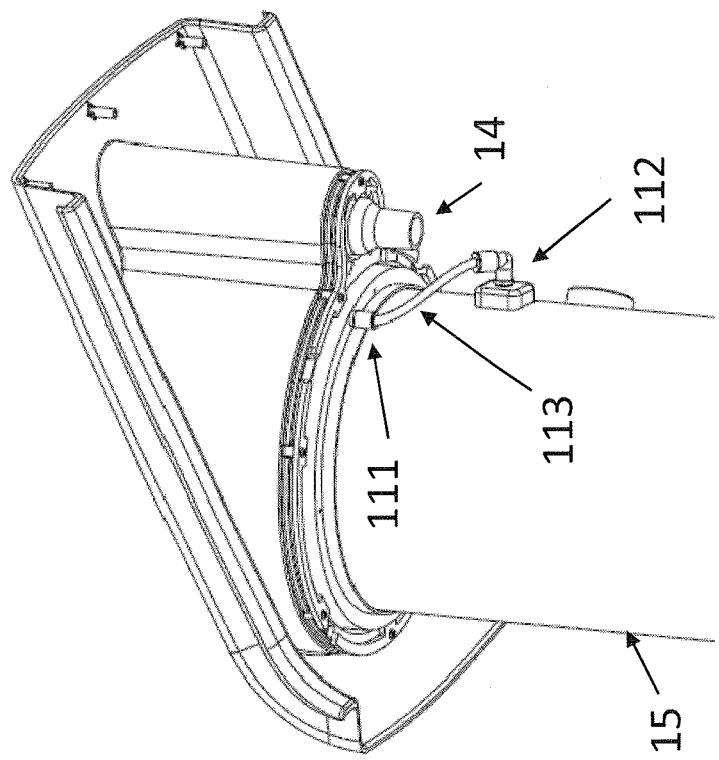
Figure 25B:
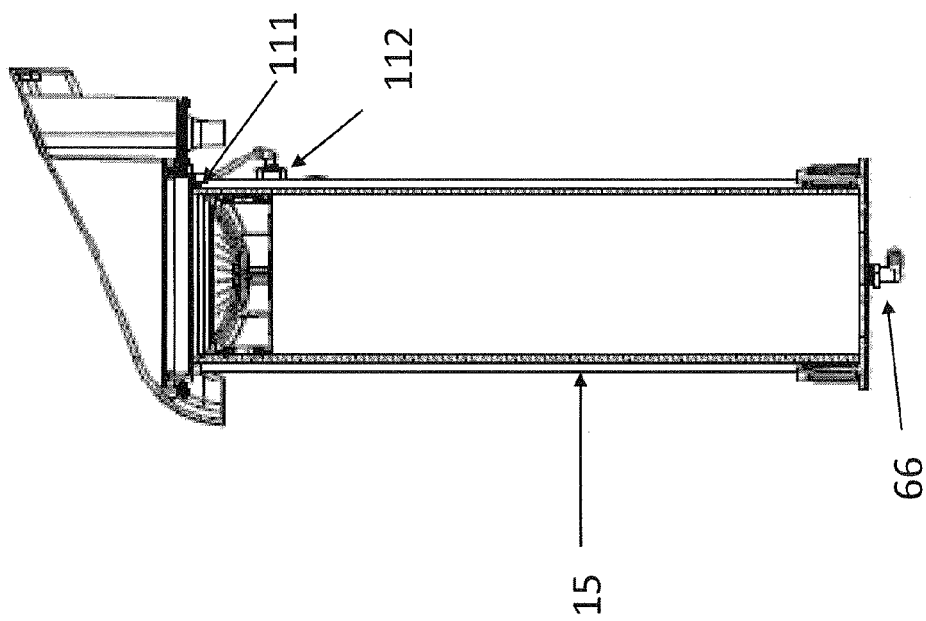
Figure 25A:
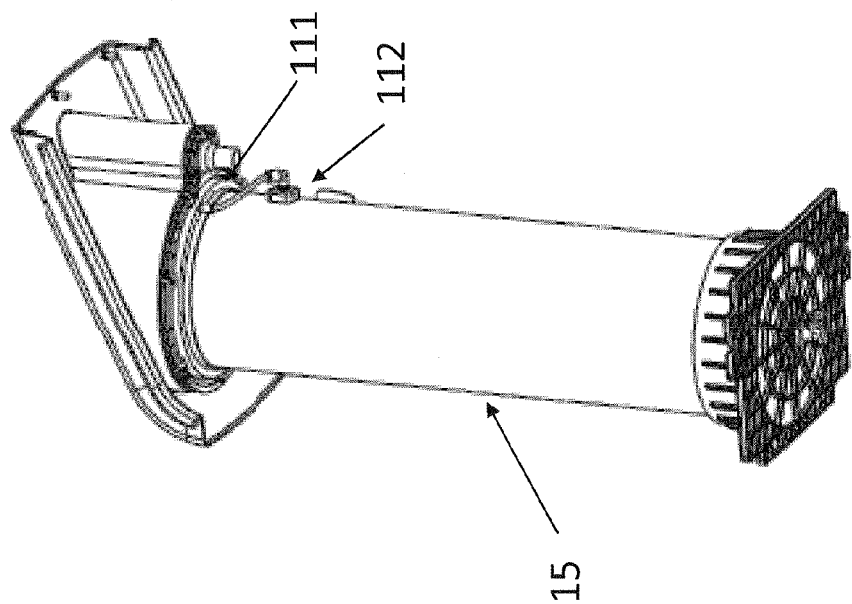

FIG. 23 illustrates exemplary aspects of illustrative vacuum connections for the liquid collection system. The piston stop feature 110 having connections 111 and 112 for regulating the pressure differential between the portions of the cavity above and below the piston 80 at a desired location. Two vacuum connections may be providing a connection 16 for providing a vacuum to the interior of the liquid collection container 30 and a vacuum connection 66 to the portion of the cavity 289 beneath the piston 80. As discussed supra, the check valve in the piston assembly may communicate the vacuum into the interstitial area between the exterior of the liquid collection liner and the interior of the cavity.

FIGS. 24A, 24B, 25A, and 25B illustrate aspects of an exemplary implementation of a main body 15 having connections 111 and 112 for regulating the pressure differential between portions of the cavity above and below the piston at a desired piston stopping point.

A main check valve 2302 may be provided between the vacuum pump 2308 and connection 16 to regulate the application of the vacuum to the interior of the liquid collection container. Likewise a piston rise check valve 2304 and a vent 2306, such as a solenoid, may be provided between the vacuum pump 2308 and connection 66. A filter unit 70 and fluid trap 2310 may be provided between the liquid collection container and the vacuum pump 2308.

The liquid collection system may further include a backup side port 2312, having an associated check valve 2314 and fluid trap 2316, for providing a backup or secondary vacuum source. The system may further include a vacuum regulator 2318 and a relief valve 2320.

Filter

In certain variations, the system 10 may include a filter unit 70 (e.g., a HEPA filter) to prevent relatively large particles from entering the vacuum pump. Referring to FIGS. 26-28, the filter unit 70 may include a filter housing comprised of an first housing portion 72 and a second housing portion 78 configured to mate with one another to define a substantially enclosed interior space for receiving a filter 75. Although FIGS. 26-28 show housing portion 72 on top and housing portion 78 on bottom, this may be reversed. For example, FIG. 26 depicts the filter 70 with housing portion 72 as a lower housing portion and housing portion 78 as an upper housing portion. In this description, housing portion 72 will be referred to as the first housing portion and housing portion 78 as the second housing portion. The first housing portion 72 may define an outlet opening 71 for connection to a vacuum, for example, and the second housing portion 78 may define one or more inlet openings 79a, 79b, and 79c for connection to various components utilizing the suction force generated by the vacuum pump. In such applications, the number of inlet openings 79a, 79b, and 79c may depend upon the number of components that require connection to the vacuum pump. For example, if the system 10 includes only one component that requires connection to the vacuum pump, the second housing portion 78 may include only one inlet opening 79a. If, however, the system includes multiple components that require connections to the vacuum pump, the second housing portion 78 may include as many inlet openings 79a, 79b, 79c as needed by the system 10. For example, as shown in FIG. 27(*b*) the second housing portion may include two inlet openings.

The first housing portion 72 and the second housing portion 78 may be joined together via one or more screws, or other attachment features, such as a suitable snap-fastening or thread-fastening mechanism or any other suitable fastening mechanism. In the exemplary illustration shown in FIG. 28, a sealing gasket 76 may be disposed between the first housing portion 72 and the second housing portion 78 to seal the interface therebetween. The first housing portion 72 and the second housing portion 78 may be readily separable to facilitate replacement of the filter 75 disposed therein.

The filter 75 may comprise a microporous (HEPA-grade) material. The filter 75 may have a generally cylindrical shape defining a hollow internal space 74 in fluid communication with the outlet opening 71 of the first housing portion 72. The filter 75 may be formed of a hydrophobic material, such as expanded PTFE on thermally fused polyester (e.g., Tetratex® ePTFE available from Donaldson Company, Inc. of Minneapolis, Minn.). The filter 75 may have hydrophobic characteristics that serve as a safety valve for preventing water from flowing into the vacuum pump, for example.

In addition, only a portion of the filter may include a hydrophobic material. For example, one side of the filter may include hydrophobic material. This, in combination with the other features, may allow the filter to continue to function even when a significant amount of liquid has entered the filter.

As shown in FIG. 28, the filter 75 may be positioned between an upper gasket 73 and an end cap 77. The upper gasket 73 may be made of polychloroprene material (e.g., neoprene) or microcellular urethane foam (e.g., Poron®), for example. The upper gasket 73 seals or partially seals the contact space between the top surface of the filter 75 and the first housing portion 72. In some exemplary variations, to enhance the sealing effect, the filter unit 70 may be configured such that, when the first housing portion 72 and the second housing portion 78 are joined together to compressibly enclose the filter unit 70, the filter 75 presses the upper gasket 73 so as to slightly compress the upper gasket 73.

The end cap 77 is configured to receive one end of the filter 75. The end cap 77 may define an annular groove 77a configured to receive the second end of the filter 75, for example, as shown in FIG. 28, for more securely holding the filter 75 in place. The end cap 77 is impermeable to fluid, thereby preventing any fluid from escaping via the first end of the filter 75. The space between the end cap 77 and the second housing portion 78 may define one or more flow paths (e.g., via reinforcement ribs extending radially). Thus, all of the fluid entering the filter unit 70 through the inlet openings 79a, 79b, 79c may flow around the end cap 77, pass through the side wall 75a of the filter 75, and exit the filter unit 70 through the internal space 74 and the outlet opening 71.

As noted above, smoke and/or gases may occur in connection with certain medical procedures. The filter is capable of filtering smoke and other undesirable gases from the air that is drawn into the liquid collection system and that passes through the filter.

Figure 29:
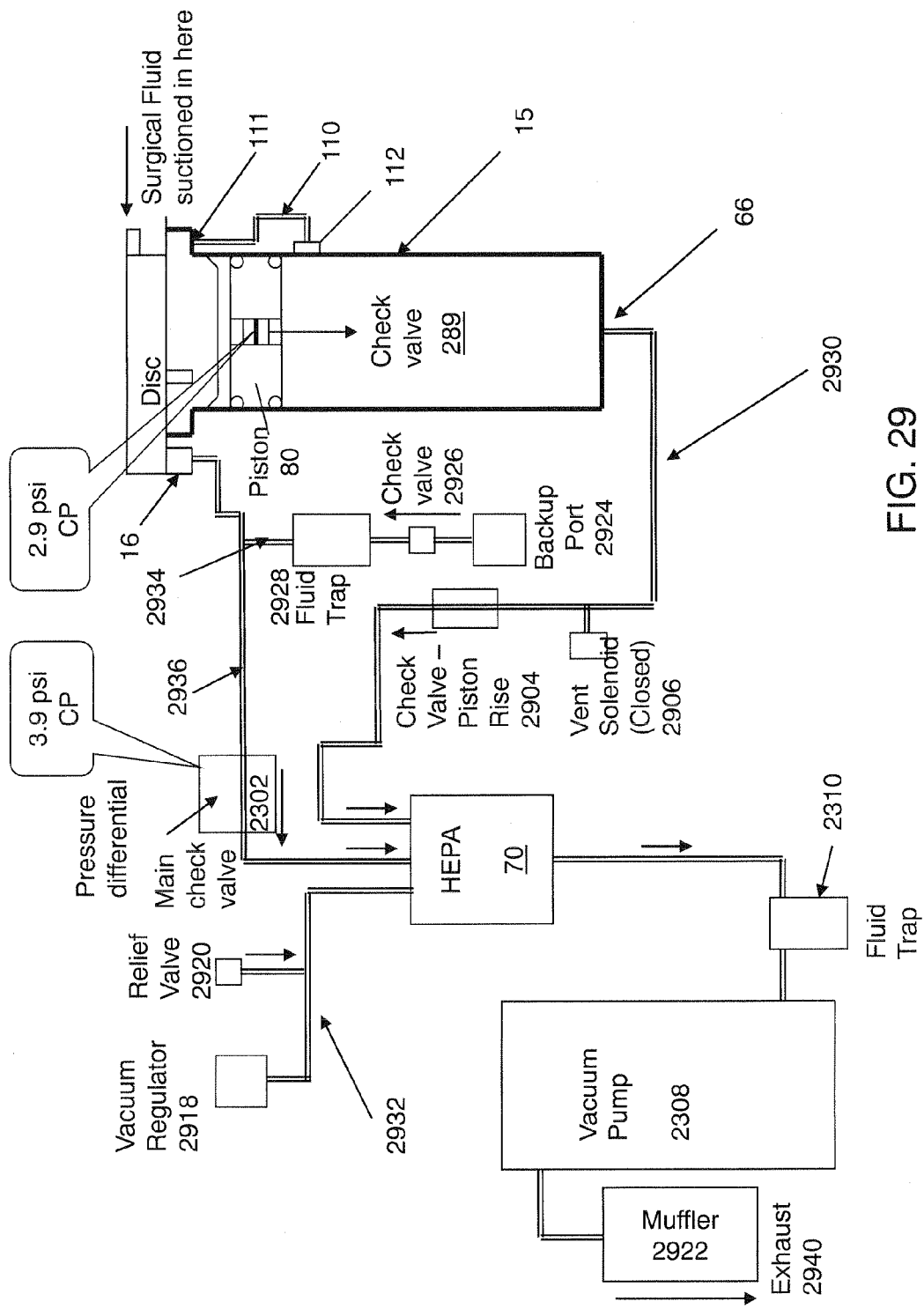
FIG. 29 illustrates a diagram of an exemplary implementation of a fluid collection system, in accordance with exemplary aspects.
Figure 30:
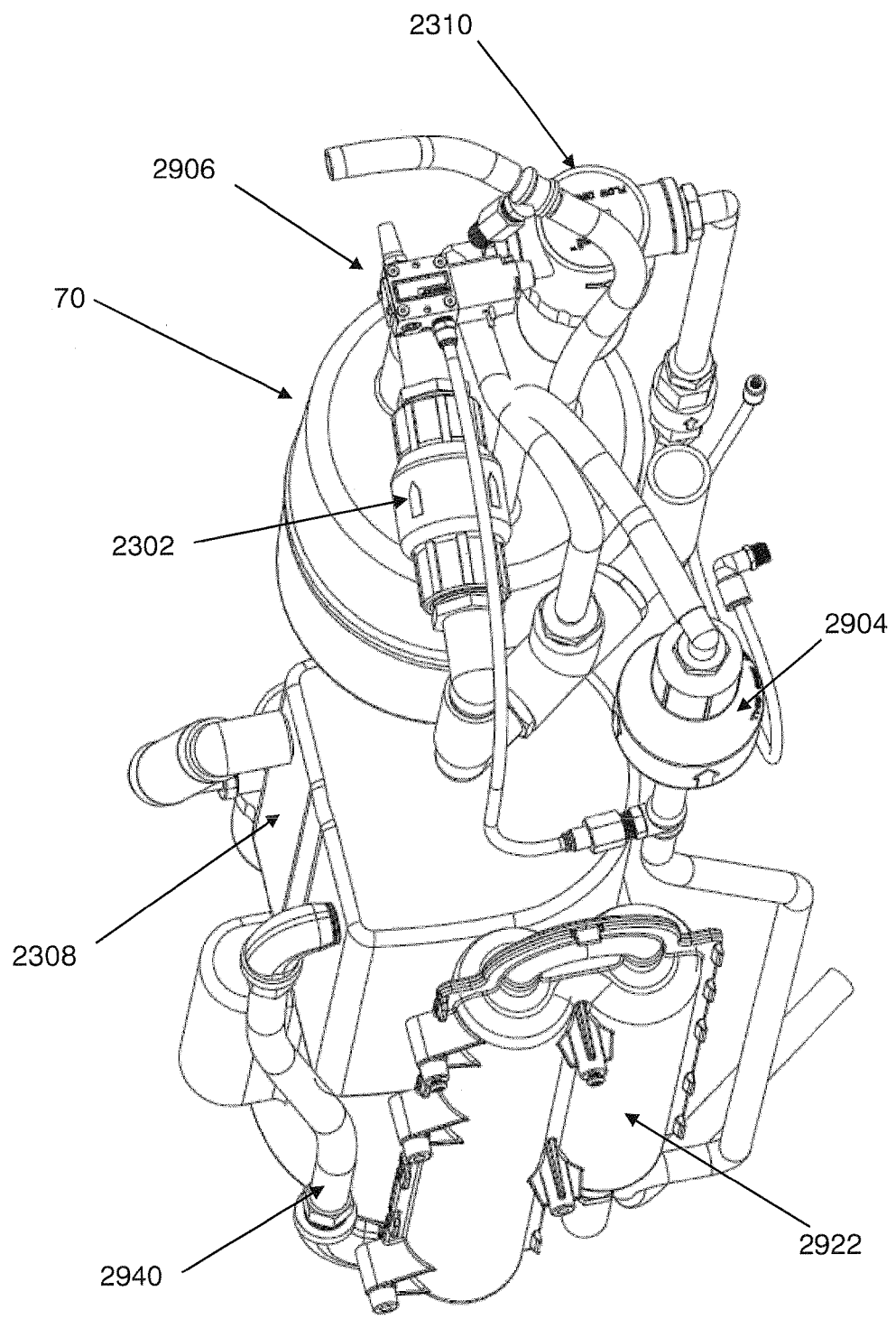
FIGS. 30-33 illustrate various views of components for the exemplary fluid collection system illustrated in FIG. 29, in accordance with exemplary aspects.
Figure 31:
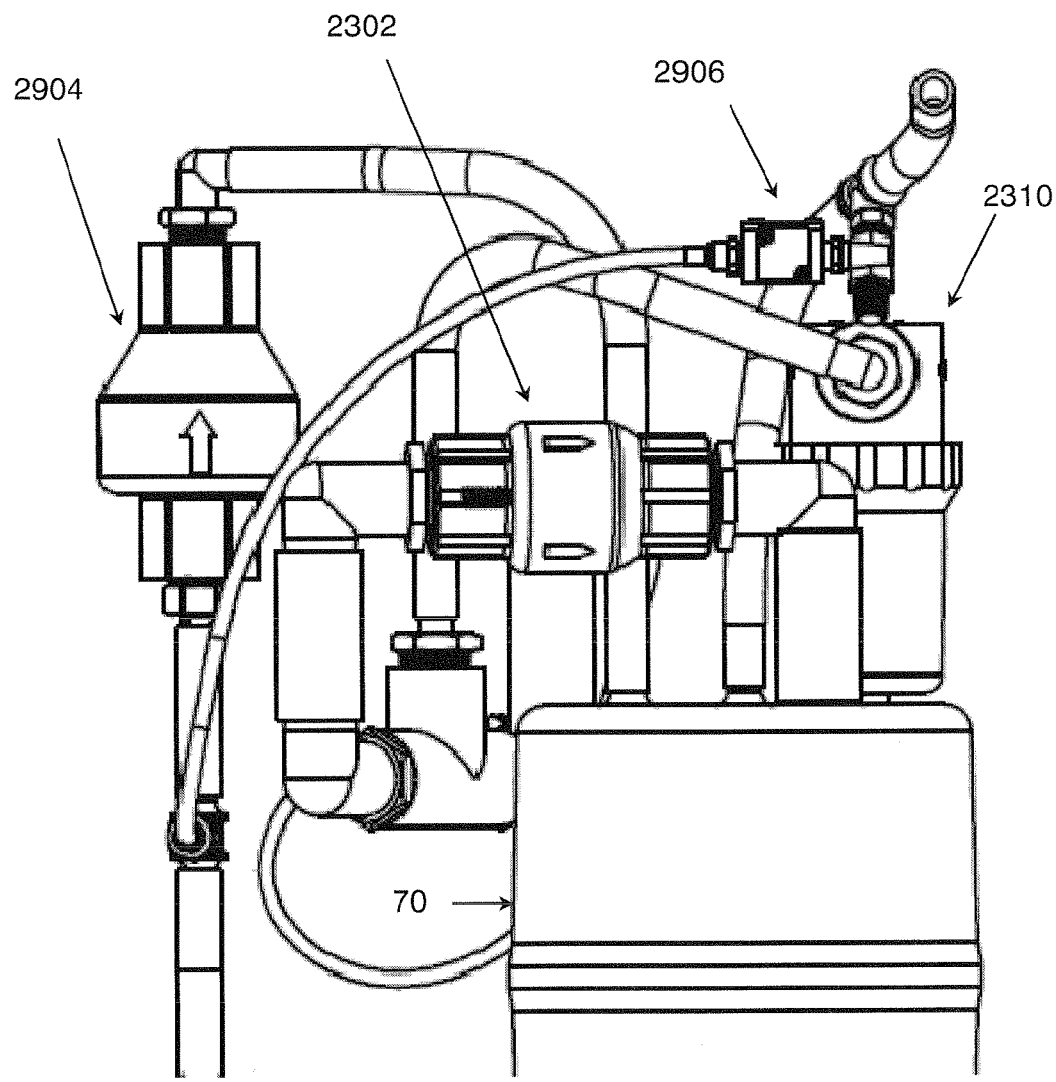
Figure 32:
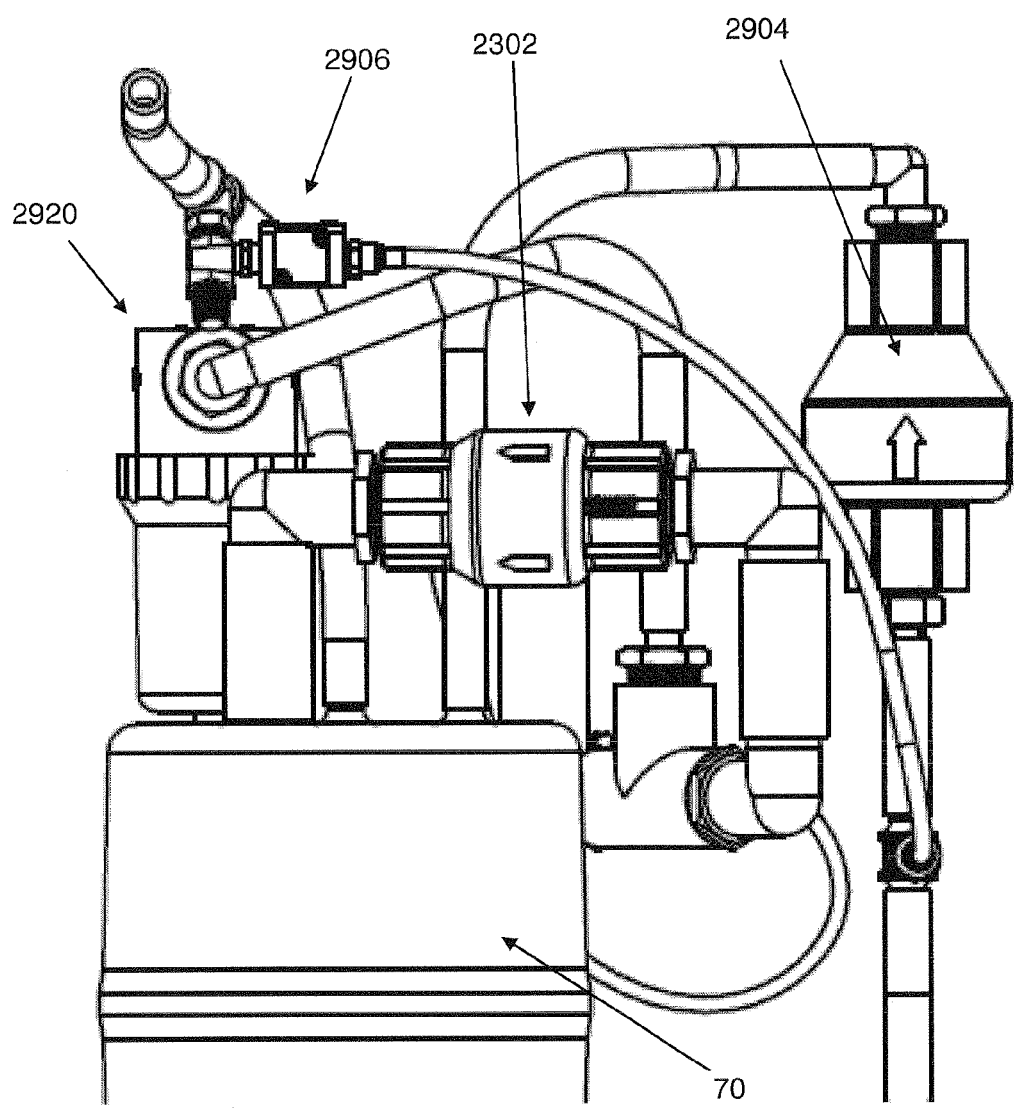
Figure 33:
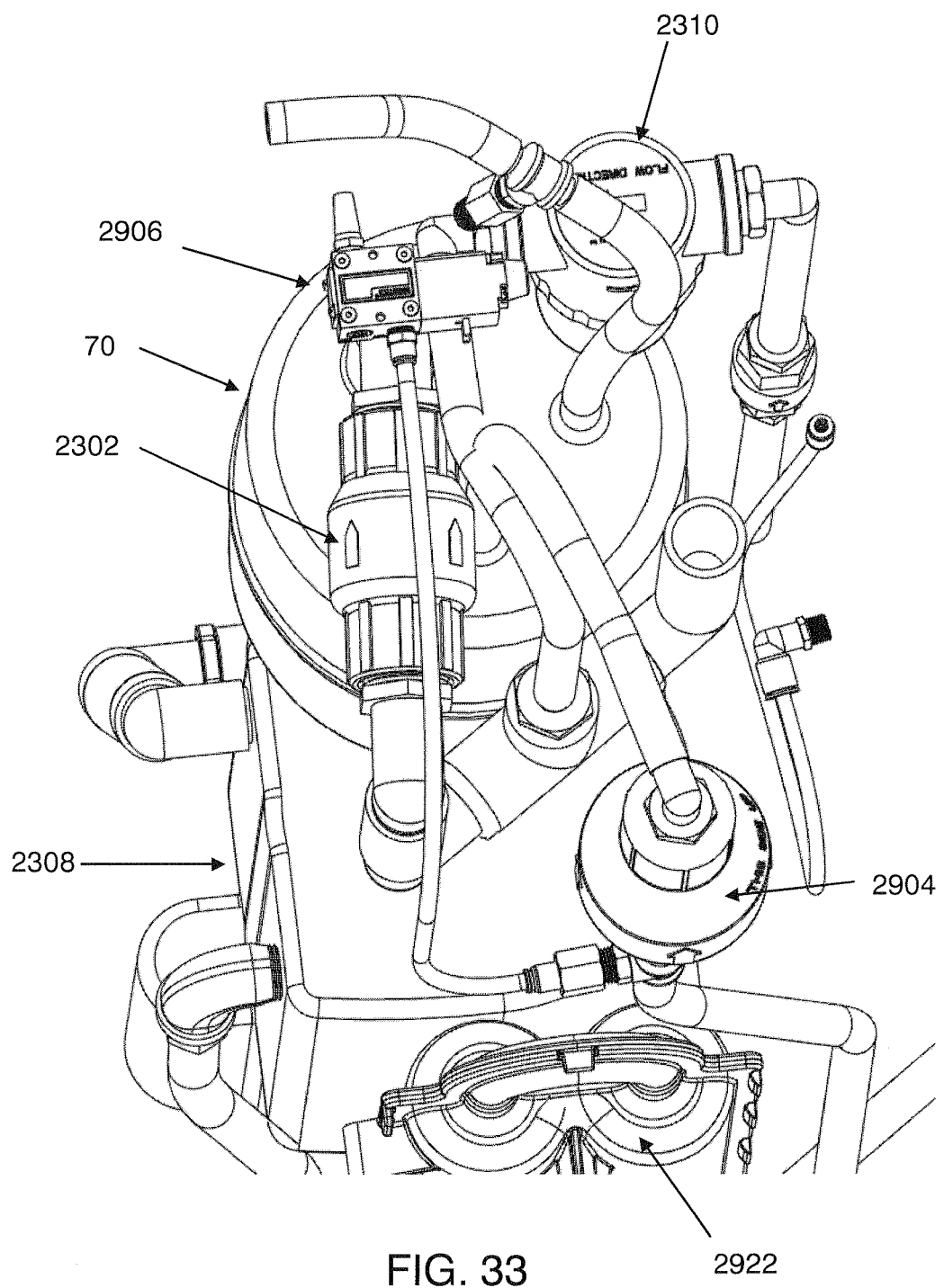

FIG. 29 illustrates another exemplary implementation of components for a liquid collection system. Various components are similar to those discussed above, e.g. in connection with FIGS. 23-25. The same reference numbers are used for these components. The liquid collection system illustrated in FIG. 29 includes a vacuum regulator 2918 and a relief valve 2920 connected to a shared line 2932 that connects to filter 70. Main check valve 2302 is connected between the suction source opening, or vacuum connection, 16 to the lid 31 and filter 70. In FIG. 23, the piston check valve 289 in the piston assembly 80 may be configured to have a cracking pressure (CP) of at least 0.25 psi, e.g. 0.29 psi, and the main check valve may be configured to have a CP of at least 0.4 psi, e.g. 0.5 psi. In FIG. 29, the piston check valve is illustrated as having a higher CP, such as above 2.5 psi, e.g. 2.9 psi CP. In addition, the main check valve may also have an increased CP, such as above 3.5 psi, e.g. 3.9 psi CP.

A vent solenoid 2906 is connected to a line 2930 extending from opening 66 at the bottom portion of the container 15 to the filter 70. A piston rise check valve 2904 is also disposed in the line between the vent solenoid 2906 and the filter 70. A line 2934 may also extend from line 2936. This line may include a fluid trap 2928, a check valve 2926, and a backup port 2924.

A muffler 2922 can be included in the exhaust line 2940 of vacuum pump 2308.

FIGS. 30-33 illustrate various views of an exemplary implementation of components for a liquid collection system having aspects similar to the diagram in FIG. 29.

While exemplary aspects have been described and illustrated with reference to one or more preferred variations thereof, it is not the intention of the applicants that these aspects be restricted to such detail. Rather, it is the intention of the applicants that aspects of the present invention be defined by all equivalents, both suggested hereby and known to those of ordinary skill in the art, of the variations falling within the scope thereof.

What is claimed is:

1. A fluid collection system configured to receive a disposable collection container, the system comprising:
    a receiving housing, the receiving housing including a cavity;
    a piston assembly positioned within the cavity and separating the cavity into a first cavity portion and a second cavity portion, the first cavity portion configured to receive the disposable collection container, the piston assembly including a piston check valve;
    a suction source connectable to the disposable collection container;
    a suction source opening, configured to communicate the suction source with the disposable collection container;
    a filter positioned between the suction source and the suction source opening;
    a first connecting line extending between the suction source opening and the filter; and
    a first check valve connected to the first connecting line between the suction source opening and the filter,
    wherein the piston check valve has a cracking pressure that is less than the cracking pressure of the first check valve.

2. The fluid collection system according to claim 1, further comprising:
    a fluid trap attached between the filter and the suction source.

3. The fluid collection system according to claim 1, wherein the cavity includes a cavity opening in the second cavity portion, the system further comprising:
    a second connecting line extending between the cavity opening and the filter;

a vent attached to the second connecting line between the cavity opening and the filter; and a second check valve connected to the second connecting line between the vent and the filter.

4. The fluid collection system according to claim 1, further comprising:
a third connecting line attached to the filter;
a vacuum regulator attached to the third connecting line; and
a relief valve attached to the third connecting line between the vacuum regulator and the filter.

5. The fluid collection system according to claim 4, further comprising:
a fourth connecting line extending from the third connecting line between the relief valve and the filter;
a port connected to the fourth connecting line;
a fluid trap connected to the fourth connecting line between the port and the filter; and
a third check valve connected to the fourth connecting line between the port and the fluid trap.

6. The fluid collection system according to claim 1, further comprising:
a fourth connecting line extending from the first connecting line between the suction source opening and the first check valve;
a port connected to the fourth connecting line;
a fluid trap connected to the fourth connecting line between the port and the first connecting line; and
a third check valve connected to the fourth connecting line between the port and the fluid trap.

7. The fluid collection system according to claim 1, further comprising:
an exhaust line extending from the suction source; and
a muffler attached to the exhaust line.

8. The fluid collection system according to claim 1, wherein the piston check valve has a cracking pressure of at least 0.29 psi.

9. The fluid collection system according to claim 8, wherein the first check valve has a cracking pressure of at least 0.5 psi.

10. The fluid collection system according to claim 9, wherein the cracking pressure of the piston check valve is greater than 2.5 psi.

11. The fluid collection system according to claim 10, wherein the cracking pressure of the first check valve is greater than 3.5 psi.

12. The fluid collection system according to claim 1, wherein the piston check valve is configured to open when pressure in the first cavity portion is a designated amount greater than pressure in the second cavity portion.

13. A fluid collection system, comprising:
a disposable collection container having a flexible liner;
a receiving housing, the receiving housing including a cavity;
a piston assembly positioned within the cavity and separating the cavity into a first cavity portion and a second cavity portion, the first cavity portion configured to receive the disposable collection container, the piston assembly including a piston check valve;
a suction source connectable to the disposable collection container;
a suction source opening, configured to communicate the suction source with the disposable collection container;
a filter positioned between the suction source and the suction source opening;
a first connecting line extending between the suction source opening and the filter; and
a first check valve connected to the first connecting line between the suction source opening and the filter,
wherein the piston check valve has a cracking pressure that is less than the cracking pressure of the first check valve.

14. The fluid collection system according to claim 13, further comprising:
a fluid trap attached between the filter and the suction source.

15. The fluid collection system according to claim 13, wherein the cavity includes a cavity opening, the system further comprising:
a second connecting line extending between the cavity opening and the filter;
a vent attached to the second connecting line between the cavity opening and the filter; and
a second check valve connected to the second connecting line between the vent and the filter.

16. The fluid collection system according to claim 13, further comprising:
a third connecting line attached to the filter;
a vacuum regulator attached to the third connecting line; and
a relief valve attached to the third connecting line between the vacuum regulator and the filter.

17. The fluid collection system according to claim 16, further comprising:
a fourth connecting line extending from the third connecting line between the relief valve and the filter;
a port connected to the fourth connecting line;
a fluid trap connected to the fourth connecting line between the port and the filter; and
a third check valve connected to the fourth connecting line between the port and the fluid trap.

18. The fluid collection system according to claim 13, further comprising:
a fourth connecting line extending from the first connecting line between the suction source opening and the first check valve;
a port connected to the fourth connecting line;
a fluid trap connected to the fourth connecting line between the port and the first connecting line; and
a third check valve connected to the fourth connecting line between the port and the fluid trap.

19. The fluid collection system according to claim 13, further comprising:
an exhaust line extending from the suction source; and
a muffler attached to the exhaust line.

20. The fluid collection system according to claim 13, wherein the piston check valve has a cracking pressure greater than 2.5 psi.

21. The fluid collection system according to claim 20, wherein the first check valve has a cracking pressure greater than 3.5 psi.

22. The fluid collection system according to claim 13, wherein the piston check valve is configured to open when pressure in the first cavity portion is a designated amount greater than pressure in the second cavity portion.

* * * * *